| (12) | United States Patent | (10) Patent No.: US 11,473,134 B2 |
|---|---|---|
| | Zhang et al. | (45) Date of Patent: Oct. 18, 2022 |

(54) METHOD FOR THE DECONVOLUTION OF NUCLEIC ACID-CONTAINING SUBSTANCE MIXTURES

(71) Applicant: Technische Universitaet Dresden, Dresden (DE)

(72) Inventors: Yixin Zhang, Dresden (DE); Jana Herrmann, Dresden (DE); Robert Wieduwild, Dresden (DE); Annett Berthold, Dresden (DE)

(73) Assignee: DYNABIND GMBH, Dresden (DE)

( * ) Notice: Subject to any disclaimer, the term of this patent is extended or adjusted under 35 U.S.C. 154(b) by 704 days.

(21) Appl. No.: 15/110,839

(22) PCT Filed: Jan. 12, 2015

(86) PCT No.: PCT/EP2015/050414
§ 371 (c)(1),
(2) Date: Jul. 11, 2016

(87) PCT Pub. No.: WO2015/104411
PCT Pub. Date: Jul. 16, 2015

(65) Prior Publication Data
US 2016/0362736 A1 Dec. 15, 2016

(30) Foreign Application Priority Data
Jan. 13, 2014 (DE) .......................... 102014200446.2

(51) Int. Cl.
*C12Q 1/6869* (2018.01)
*G16B 30/00* (2019.01)

(52) U.S. Cl.
CPC ........... *C12Q 1/6869* (2013.01); *G16B 30/00* (2019.02)

(58) Field of Classification Search
CPC .............................. G16B 30/00; C12Q 1/6869
(Continued)

(56) References Cited

FOREIGN PATENT DOCUMENTS

| WO | WO 95/18623 | 7/1995 |
| WO | WO 2013/137737 A1 | 9/2013 |

OTHER PUBLICATIONS

Lin, C., Jungmann, R., Leifer, A. et al. Submicrometre geometrically encoded fluorescent barcodes self-assembled from DNA. Nature Chem 4, 832-839 (2012) (Year: 2012).*

(Continued)

*Primary Examiner* — Soren Harward
*Assistant Examiner* — Guozhen Liu
(74) *Attorney, Agent, or Firm* — Jacobson Holman PLLC

(57) ABSTRACT

A method for the deconvolution of nucleic acid-containing substance mixtures using synthetically generated target nucleotide sequences. Starting from a plurality of nucleotides,, a plurality of different target nucleotide sequences (TNS) is generated according to a predetermined algorithm. At least one of the TNS generated is associated with at least one substance or substance combination and chemically coupled thereto. At least one substance mixture to be analysed and having at least two different TNS is provided and is sequenced according to a sequencing method., at the same time all TNS contained in the substance mixture are detected in a common sequence spectrum. To facilitate the deconvolution, the sequence spectra of a substance mixture should be deducted/subtracted from each other prior to and after a selection experiment.

10 Claims, 4 Drawing Sheets

Figure 4A:
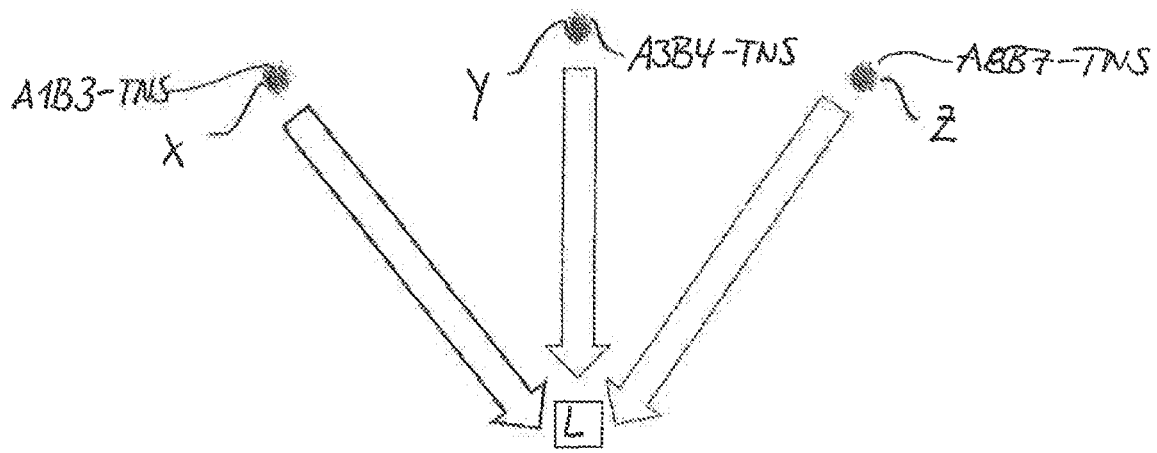

Specification includes a Sequence Listing.

(58) Field of Classification Search
USPC .......................................................... 703/11
See application file for complete search history.

(56) References Cited

OTHER PUBLICATIONS

Geiss, G., Bumgarner, R., Birditt, B. et al. Direct multiplexed measurement of gene expression with color-coded probe pairs. Nat Biotechnol 26, 317-325 (2008). (Year: 2008).*

Jiyoun Lee, Matthew Bogyo: Target deconvolution techniques in modern phenotypic profiling, Current Opinion in Chemical Biology, vol. 17, Issue 1, Feb. 2013, pp. 118-126 (Year: 2013).*

Faircloth et al., "Large sets of edit-metric sequence Identification tags to facilitate large-scale multiplexing of reads from massively parallel sequencing", Feb. 13, 2011.

Krishnan et al., "Barcodes for DNA sequencing with guaranteed error correction capability", Electronic Letters, vol. 47, No. 4, pp. 236-237, Feb. 17, 2011.

Bystrykh et al., "Generalized DNA Barcode Design Based on Hamming Codes", PLOS ONE, vol. 7, No. 5, p. e36852, May 17, 2012.

Buschmann et al., "Levenshtein error-correcting barcodes for multiplexed DNA sequencing", BMC Bioformatics, Bd. 14, Nr. 1, pp. 1-10, Sep. 11, 2013.

Leimbacher et al., "Discovery of Small-Molecule Interleukin-2 Inhibitors from a DNA-Encloded Chemical Library", Chem. Eur. J. Bd. 18, Nr. 25, Jun. 18, 2012.

Frank, "BARCRAWL and BARTAB: software tools for the design and implementation of barcoded primers for highly multiplexed DNA sequencing", BMC Bioinfo, Bd. 10, Nr. 1, Jan. 1, 2009.

Xu et al., "Design of 240,000 orthogonal 25mer DNA barcode probes", Proceedings of the National Academy of Sciences, Bd. 106, Nr. 7, Feb. 17, 2009.

Buller et al., "High-throughput sequencing for the identificatin of binding molecules from DNA-encoded chemical libraries", Bioorganic & Med Chem, Bd. 20, Nr. 14, Jul. 15, 2010.

Kleiner et al., "Small-molecule discovery from DNA-encoded chemical libraries", Chemical Socociety Reviews, Bd. 40, Nr. 12, Jun. 14, 2011.

Erb et al., "Recursive deconvolution of combinatoria chemical libraries", Proceedings National Academy of Sciences, vol. 91, pp. 11422-11426, Nov. 1994.

* cited by examiner

Fig. 1

$N_\alpha$ ........ $N_\beta$ ---- X
z-a-a-d-d-e-a-a-d-d-e-a-d-e

TNS according to the following algorithm

Operation-z:  A/C/G/T

Operation-a:  A->G/T;   C->G/T;   G->A/C;   T->A/C

Operation-d:  A->C/T;   C->A/G;   G->A/T;   T->C/G

Operation-e:  A->C/G;   C->A/T;   G->C/T;   T->A/G

Number of different TNS per number of sequence differences

Difference of 0 -----0
Difference of 1 -----0
Difference of 2 -----0
Difference of 3 -----0
Difference of 4 -----0
Difference of 5 -----0
Difference of 6 -----820
Difference of 7 -----1141
Difference of 8 -----1569
Difference of 9 -----2269
Difference of 10 -----3027
Difference of 11 -----3544
Difference of 12 -----3382
Difference of 13 -----2535
Difference of 14 -----1216

10

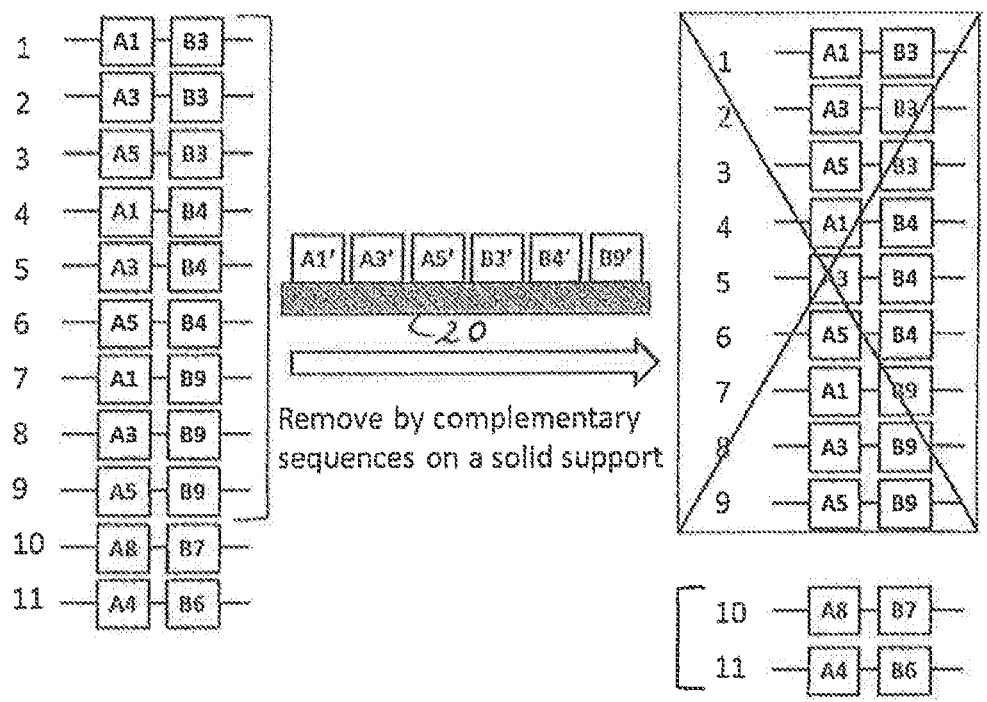

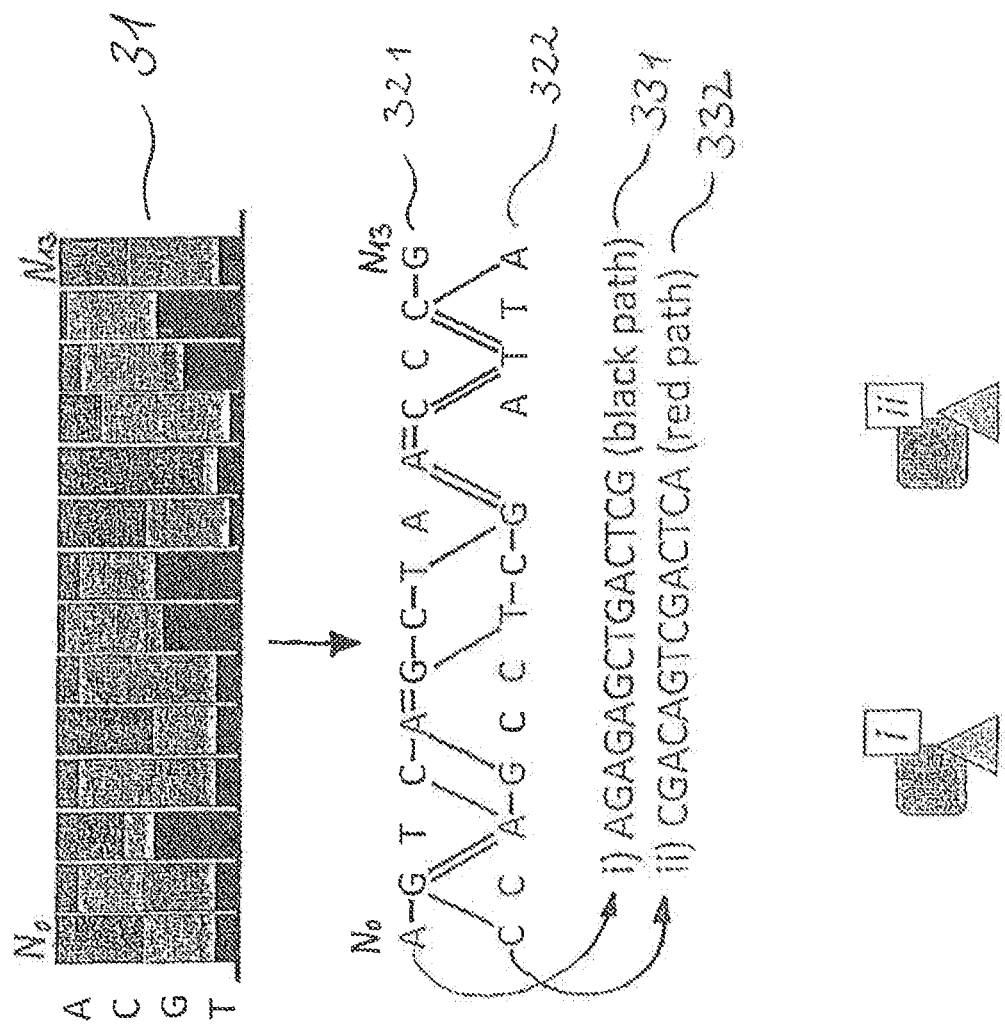

SEQUENCE LISTING

```
<160> NUMBER OF SEQ ID NOS: 198

<210> SEQ ID NO 1
<211> LENGTH: 14
<212> TYPE: DNA
<213> ORGANISM: Artificial Sequence
<220> FEATURE:
<223> OTHER INFORMATION: Synthesized

<400> SEQUENCE: 1
gcgatgagac atgt                                                    14

<210> SEQ ID NO 2
<211> LENGTH: 14
<212> TYPE: DNA
<213> ORGANISM: Artificial Sequence
<220> FEATURE:
<223> OTHER INFORMATION: Synthesized

<400> SEQUENCE: 2
atcatatacg tata                                                    14

<210> SEQ ID NO 3
<211> LENGTH: 14
<212> TYPE: DNA
<213> ORGANISM: Artificial Sequence
<220> FEATURE:
<223> OTHER INFORMATION: Synthesized

<400> SEQUENCE: 3
tagacatcat agag                                                    14

<210> SEQ ID NO 4
<211> LENGTH: 14
```

```
<212> TYPE: DNA
<213> ORGANISM: Artificial Sequence
<220> FEATURE:
<223> OTHER INFORMATION: Synthesized

<400> SEQUENCE: 4
tatgtgctcg cgag                                                         14

<210> SEQ ID NO 5
<211> LENGTH: 14
<212> TYPE: DNA
<213> ORGANISM: Artificial Sequence
<220> FEATURE:
<223> OTHER INFORMATION: Synthesized

<400> SEQUENCE: 5
agatgctatg tcac                                                         14

<210> SEQ ID NO 6
<211> LENGTH: 14
<212> TYPE: DNA
<213> ORGANISM: Artificial Sequence
<220> FEATURE:
<223> OTHER INFORMATION: Synthesized

<400> SEQUENCE: 6
tctcgtagtc tcgt                                                         14

<210> SEQ ID NO 7
<211> LENGTH: 14
<212> TYPE: DNA
<213> ORGANISM: Artificial Sequence
<220> FEATURE:
<223> OTHER INFORMATION: Synthesized

<400> SEQUENCE: 7
tcgatgatca ctct                                                         14

<210> SEQ ID NO 8
<211> LENGTH: 14
<212> TYPE: DNA
<213> ORGANISM: Artificial Sequence
<220> FEATURE:
<223> OTHER INFORMATION: Synthesized

<400> SEQUENCE: 8
gctcagctgt gcag                                                         14

<210> SEQ ID NO 9
<211> LENGTH: 14
<212> TYPE: DNA
<213> ORGANISM: Artificial Sequence
<220> FEATURE:
<223> OTHER INFORMATION: Synthesized

<400> SEQUENCE: 9
ctcgagatcg ctgc                                                         14

<210> SEQ ID NO 10
<211> LENGTH: 14
<212> TYPE: DNA
<213> ORGANISM: Artificial Sequence
<220> FEATURE:
<223> OTHER INFORMATION: Synthesized

<400> SEQUENCE: 10
```

```
cgcactagat gcgt                                                     14

<210> SEQ ID NO 11
<211> LENGTH: 14
<212> TYPE: DNA
<213> ORGANISM: Artificial Sequence
<220> FEATURE:
<223> OTHER INFORMATION: Synthesized

<400> SEQUENCE: 11
gctcgcgcga gcac                                                     14

<210> SEQ ID NO 12
<211> LENGTH: 14
<212> TYPE: DNA
<213> ORGANISM: Artificial Sequence
<220> FEATURE:
<223> OTHER INFORMATION: Synthesized

<400> SEQUENCE: 12
agcgtgagtc tcag                                                     14

<210> SEQ ID NO 13
<211> LENGTH: 14
<212> TYPE: DNA
<213> ORGANISM: Artificial Sequence
<220> FEATURE:
<223> OTHER INFORMATION: Synthesized

<400> SEQUENCE: 13
ctcgactatc agac                                                     14

<210> SEQ ID NO 14
<211> LENGTH: 14
<212> TYPE: DNA
<213> ORGANISM: Artificial Sequence
<220> FEATURE:
<223> OTHER INFORMATION: Synthesized

<400> SEQUENCE: 14
cgatgctcat agta                                                     14

<210> SEQ ID NO 15
<211> LENGTH: 14
<212> TYPE: DNA
<213> ORGANISM: Artificial Sequence
<220> FEATURE:
<223> OTHER INFORMATION: Synthesized

<400> SEQUENCE: 15
atcgacgcat gcag                                                     14

<210> SEQ ID NO 16
<211> LENGTH: 14
<212> TYPE: DNA
<213> ORGANISM: Artificial Sequence
<220> FEATURE:
<223> OTHER INFORMATION: Synthesized

<400> SEQUENCE: 16
gagtgcgatc agag                                                     14

<210> SEQ ID NO 17
<211> LENGTH: 14
<212> TYPE: DNA
<213> ORGANISM: Artificial Sequence
```

```
<220> FEATURE:
<223> OTHER INFORMATION: Synthesized

<400> SEQUENCE: 17
ctacactcac taca                                                      14

<210> SEQ ID NO 18
<211> LENGTH: 14
<212> TYPE: DNA
<213> ORGANISM: Artificial Sequence
<220> FEATURE:
<223> OTHER INFORMATION: Synthesized

<400> SEQUENCE: 18
tatcgtcgat gata                                                      14

<210> SEQ ID NO 19
<211> LENGTH: 14
<212> TYPE: DNA
<213> ORGANISM: Artificial Sequence
<220> FEATURE:
<223> OTHER INFORMATION: Synthesized

<400> SEQUENCE: 19
tctgtatatc tcac                                                      14

<210> SEQ ID NO 20
<211> LENGTH: 14
<212> TYPE: DNA
<213> ORGANISM: Artificial Sequence
<220> FEATURE:
<223> OTHER INFORMATION: Synthesized

<400> SEQUENCE: 20
gatcactcgt atca                                                      14

<210> SEQ ID NO 21
<211> LENGTH: 14
<212> TYPE: DNA
<213> ORGANISM: Artificial Sequence
<220> FEATURE:
<223> OTHER INFORMATION: Synthesized

<400> SEQUENCE: 21
agcatagcga cgta                                                      14

<210> SEQ ID NO 22
<211> LENGTH: 14
<212> TYPE: DNA
<213> ORGANISM: Artificial Sequence
<220> FEATURE:
<223> OTHER INFORMATION: Synthesized

<400> SEQUENCE: 22
tctgagcgat agta                                                      14

<210> SEQ ID NO 23
<211> LENGTH: 14
<212> TYPE: DNA
<213> ORGANISM: Artificial Sequence
<220> FEATURE:
<223> OTHER INFORMATION: Synthesized

<400> SEQUENCE: 23
atatctctga cgtg                                                      14
```

```
<210> SEQ ID NO 24
<211> LENGTH: 14
<212> TYPE: DNA
<213> ORGANISM: Artificial Sequence
<220> FEATURE:
<223> OTHER INFORMATION: Synthesized

<400> SEQUENCE: 24
gagtctagac tcag                                                         14

<210> SEQ ID NO 25
<211> LENGTH: 14
<212> TYPE: DNA
<213> ORGANISM: Artificial Sequence
<220> FEATURE:
<223> OTHER INFORMATION: Synthesized

<400> SEQUENCE: 25
gagtgtagtg taca                                                         14

<210> SEQ ID NO 26
<211> LENGTH: 14
<212> TYPE: DNA
<213> ORGANISM: Artificial Sequence
<220> FEATURE:
<223> OTHER INFORMATION: Synthesized

<400> SEQUENCE: 26
gctgtgctga gata                                                         14

<210> SEQ ID NO 27
<211> LENGTH: 14
<212> TYPE: DNA
<213> ORGANISM: Artificial Sequence
<220> FEATURE:
<223> OTHER INFORMATION: Synthesized

<400> SEQUENCE: 27
ctacgtatgt atct                                                         14

<210> SEQ ID NO 28
<211> LENGTH: 14
<212> TYPE: DNA
<213> ORGANISM: Artificial Sequence
<220> FEATURE:
<223> OTHER INFORMATION: Synthesized

<400> SEQUENCE: 28
tatcgcgacg tata                                                         14

<210> SEQ ID NO 29
<211> LENGTH: 14
<212> TYPE: DNA
<213> ORGANISM: Artificial Sequence
<220> FEATURE:
<223> OTHER INFORMATION: Synthesized

<400> SEQUENCE: 29
gagactcgtg cgtg                                                         14

<210> SEQ ID NO 30
<211> LENGTH: 14
<212> TYPE: DNA
<213> ORGANISM: Artificial Sequence
<220> FEATURE:
<223> OTHER INFORMATION: Synthesized
```

<400> SEQUENCE: 30
tatcgctcac agac                                                       14

<210> SEQ ID NO 31
<211> LENGTH: 14
<212> TYPE: DNA
<213> ORGANISM: Artificial Sequence
<220> FEATURE:
<223> OTHER INFORMATION: Synthesized

<400> SEQUENCE: 31
tatcgctaca gcgt                                                       14

<210> SEQ ID NO 32
<211> LENGTH: 14
<212> TYPE: DNA
<213> ORGANISM: Artificial Sequence
<220> FEATURE:
<223> OTHER INFORMATION: Synthesized

<400> SEQUENCE: 32
ctcactctca gcag                                                       14

<210> SEQ ID NO 33
<211> LENGTH: 14
<212> TYPE: DNA
<213> ORGANISM: Artificial Sequence
<220> FEATURE:
<223> OTHER INFORMATION: Synthesized

<400> SEQUENCE: 33
gatcagctca ctgt                                                       14

<210> SEQ ID NO 34
<211> LENGTH: 14
<212> TYPE: DNA
<213> ORGANISM: Artificial Sequence
<220> FEATURE:
<223> OTHER INFORMATION: Synthesized

<400> SEQUENCE: 34
agcgtgctgt atgt                                                       14

<210> SEQ ID NO 35
<211> LENGTH: 14
<212> TYPE: DNA
<213> ORGANISM: Artificial Sequence
<220> FEATURE:
<223> OTHER INFORMATION: Synthesized

<400> SEQUENCE: 35
cgacgcgcga cgag                                                       14

<210> SEQ ID NO 36
<211> LENGTH: 14
<212> TYPE: DNA
<213> ORGANISM: Artificial Sequence
<220> FEATURE:
<223> OTHER INFORMATION: Synthesized

<400> SEQUENCE: 36
tcgatagaca gatg                                                       14

<210> SEQ ID NO 37

```
<211> LENGTH: 14
<212> TYPE: DNA
<213> ORGANISM: Artificial Sequence
<220> FEATURE:
<223> OTHER INFORMATION: Synthesized

<400> SEQUENCE: 37
gcgatgctgt atca                                                         14

<210> SEQ ID NO 38
<211> LENGTH: 14
<212> TYPE: DNA
<213> ORGANISM: Artificial Sequence
<220> FEATURE:
<223> OTHER INFORMATION: Synthesized

<400> SEQUENCE: 38
ctacgcgatg ctgc                                                         14

<210> SEQ ID NO 39
<211> LENGTH: 14
<212> TYPE: DNA
<213> ORGANISM: Artificial Sequence
<220> FEATURE:
<223> OTHER INFORMATION: Synthesized

<400> SEQUENCE: 39
cgcacagcac agtg                                                         14

<210> SEQ ID NO 40
<211> LENGTH: 14
<212> TYPE: DNA
<213> ORGANISM: Artificial Sequence
<220> FEATURE:
<223> OTHER INFORMATION: Synthesized

<400> SEQUENCE: 40
gcgtcagatg ctca                                                         14

<210> SEQ ID NO 41
<211> LENGTH: 14
<212> TYPE: DNA
<213> ORGANISM: Artificial Sequence
<220> FEATURE:
<223> OTHER INFORMATION: Synthesized

<400> SEQUENCE: 41
tagtctcgat gcgc                                                         14

<210> SEQ ID NO 42
<211> LENGTH: 14
<212> TYPE: DNA
<213> ORGANISM: Artificial Sequence
<220> FEATURE:
<223> OTHER INFORMATION: Synthesized

<400> SEQUENCE: 42
atcacagcat gaca                                                         14

<210> SEQ ID NO 43
<211> LENGTH: 14
<212> TYPE: DNA
<213> ORGANISM: Artificial Sequence
<220> FEATURE:
<223> OTHER INFORMATION: Synthesized

<400> SEQUENCE: 43
```

```
ctatgctaca cgac                                                     14

<210> SEQ ID NO 44
<211> LENGTH: 14
<212> TYPE: DNA
<213> ORGANISM: Artificial Sequence
<220> FEATURE:
<223> OTHER INFORMATION: Synthesized

<400> SEQUENCE: 44
cgcacagatg tcgt                                                     14

<210> SEQ ID NO 45
<211> LENGTH: 14
<212> TYPE: DNA
<213> ORGANISM: Artificial Sequence
<220> FEATURE:
<223> OTHER INFORMATION: Synthesized

<400> SEQUENCE: 45
agacagatga gact                                                     14

<210> SEQ ID NO 46
<211> LENGTH: 14
<212> TYPE: DNA
<213> ORGANISM: Artificial Sequence
<220> FEATURE:
<223> OTHER INFORMATION: Synthesized

<400> SEQUENCE: 46
atatcatcgt atgt                                                     14

<210> SEQ ID NO 47
<211> LENGTH: 14
<212> TYPE: DNA
<213> ORGANISM: Artificial Sequence
<220> FEATURE:
<223> OTHER INFORMATION: Synthesized

<400> SEQUENCE: 47
gatgtagcac tact                                                     14

<210> SEQ ID NO 48
<211> LENGTH: 14
<212> TYPE: DNA
<213> ORGANISM: Artificial Sequence
<220> FEATURE:
<223> OTHER INFORMATION: Synthesized

<400> SEQUENCE: 48
tatgtatcga ctct                                                     14

<210> SEQ ID NO 49
<211> LENGTH: 14
<212> TYPE: DNA
<213> ORGANISM: Artificial Sequence
<220> FEATURE:
<223> OTHER INFORMATION: Synthesized

<400> SEQUENCE: 49
cgacagagac agtg                                                     14

<210> SEQ ID NO 50
<211> LENGTH: 14
<212> TYPE: DNA
```

```
<213> ORGANISM: Artificial Sequence
<220> FEATURE:
<223> OTHER INFORMATION: Synthesized

<400> SEQUENCE: 50
ctcgtagatc atgt                                                         14

<210> SEQ ID NO 51
<211> LENGTH: 14
<212> TYPE: DNA
<213> ORGANISM: Artificial Sequence
<220> FEATURE:
<223> OTHER INFORMATION: Synthesized

<400> SEQUENCE: 51
cgacgtctcg tcgt                                                         14

<210> SEQ ID NO 52
<211> LENGTH: 14
<212> TYPE: DNA
<213> ORGANISM: Artificial Sequence
<220> FEATURE:
<223> OTHER INFORMATION: Synthesized

<400> SEQUENCE: 52
tagtgcgacg ctct                                                         14

<210> SEQ ID NO 53
<211> LENGTH: 14
<212> TYPE: DNA
<213> ORGANISM: Artificial Sequence
<220> FEATURE:
<223> OTHER INFORMATION: Synthesized

<400> SEQUENCE: 53
gagacagaca ctgt                                                         14

<210> SEQ ID NO 54
<211> LENGTH: 14
<212> TYPE: DNA
<213> ORGANISM: Artificial Sequence
<220> FEATURE:
<223> OTHER INFORMATION: Synthesized

<400> SEQUENCE: 54
gcgactcgat gaca                                                         14

<210> SEQ ID NO 55
<211> LENGTH: 14
<212> TYPE: DNA
<213> ORGANISM: Artificial Sequence
<220> FEATURE:
<223> OTHER INFORMATION: Synthesized

<400> SEQUENCE: 55
agacacgcgt gata                                                         14

<210> SEQ ID NO 56
<211> LENGTH: 14
<212> TYPE: DNA
<213> ORGANISM: Artificial Sequence
<220> FEATURE:
<223> OTHER INFORMATION: Synthesized

<400> SEQUENCE: 56
atcatatcac tcag                                                         14
```

<210> SEQ ID NO 57
<211> LENGTH: 14
<212> TYPE: DNA
<213> ORGANISM: Artificial Sequence
<220> FEATURE:
<223> OTHER INFORMATION: Synthesized

<400> SEQUENCE: 57
gatgtatcat atgc                                                       14

<210> SEQ ID NO 58
<211> LENGTH: 14
<212> TYPE: DNA
<213> ORGANISM: Artificial Sequence
<220> FEATURE:
<223> OTHER INFORMATION: Synthesized

<400> SEQUENCE: 58
gctcgtcgtc agta                                                       14

<210> SEQ ID NO 59
<211> LENGTH: 14
<212> TYPE: DNA
<213> ORGANISM: Artificial Sequence
<220> FEATURE:
<223> OTHER INFORMATION: Synthesized

<400> SEQUENCE: 59
cgatgtatca cgta                                                       14

<210> SEQ ID NO 60
<211> LENGTH: 14
<212> TYPE: DNA
<213> ORGANISM: Artificial Sequence
<220> FEATURE:
<223> OTHER INFORMATION: Synthesized

<400> SEQUENCE: 60
ctatgctcgt gact                                                       14

<210> SEQ ID NO 61
<211> LENGTH: 14
<212> TYPE: DNA
<213> ORGANISM: Artificial Sequence
<220> FEATURE:
<223> OTHER INFORMATION: Synthesized

<400> SEQUENCE: 61
tatgtgagac tata                                                       14

<210> SEQ ID NO 62
<211> LENGTH: 14
<212> TYPE: DNA
<213> ORGANISM: Artificial Sequence
<220> FEATURE:
<223> OTHER INFORMATION: Synthesized

<400> SEQUENCE: 62
ctcgtgagtc agta                                                       14

<210> SEQ ID NO 63
<211> LENGTH: 14
<212> TYPE: DNA
<213> ORGANISM: Artificial Sequence
<220> FEATURE:

<223> OTHER INFORMATION: Synthesized

<400> SEQUENCE: 63
tctgacgcga gact                                                        14

<210> SEQ ID NO 64
<211> LENGTH: 14
<212> TYPE: DNA
<213> ORGANISM: Artificial Sequence
<220> FEATURE:
<223> OTHER INFORMATION: Synthesized

<400> SEQUENCE: 64
tagtctatga ctgc                                                        14

<210> SEQ ID NO 65
<211> LENGTH: 14
<212> TYPE: DNA
<213> ORGANISM: Artificial Sequence
<220> FEATURE:
<223> OTHER INFORMATION: Synthesized

<400> SEQUENCE: 65
cgcgactatg ctgt                                                        14

<210> SEQ ID NO 66
<211> LENGTH: 14
<212> TYPE: DNA
<213> ORGANISM: Artificial Sequence
<220> FEATURE:
<223> OTHER INFORMATION: Synthesized

<400> SEQUENCE: 66
gatcgtatgt gcgc                                                        14

<210> SEQ ID NO 67
<211> LENGTH: 14
<212> TYPE: DNA
<213> ORGANISM: Artificial Sequence
<220> FEATURE:
<223> OTHER INFORMATION: Synthesized

<400> SEQUENCE: 67
agatcataca gact                                                        14

<210> SEQ ID NO 68
<211> LENGTH: 14
<212> TYPE: DNA
<213> ORGANISM: Artificial Sequence
<220> FEATURE:
<223> OTHER INFORMATION: Synthesized

<400> SEQUENCE: 68
tatgagcgtg ctgc                                                        14

<210> SEQ ID NO 69
<211> LENGTH: 14
<212> TYPE: DNA
<213> ORGANISM: Artificial Sequence
<220> FEATURE:
<223> OTHER INFORMATION: Synthesized

<400> SEQUENCE: 69
tcgatatatg ctgc                                                        14

```
<210> SEQ ID NO 70
<211> LENGTH: 14
<212> TYPE: DNA
<213> ORGANISM: Artificial Sequence
<220> FEATURE:
<223> OTHER INFORMATION: Synthesized

<400> SEQUENCE: 70
agcactctcg tatg                                                        14

<210> SEQ ID NO 71
<211> LENGTH: 14
<212> TYPE: DNA
<213> ORGANISM: Artificial Sequence
<220> FEATURE:
<223> OTHER INFORMATION: Synthesized

<400> SEQUENCE: 71
ctatcatatg cgta                                                        14

<210> SEQ ID NO 72
<211> LENGTH: 14
<212> TYPE: DNA
<213> ORGANISM: Artificial Sequence
<220> FEATURE:
<223> OTHER INFORMATION: Synthesized

<400> SEQUENCE: 72
tcgtgtcgtg ctgt                                                        14

<210> SEQ ID NO 73
<211> LENGTH: 14
<212> TYPE: DNA
<213> ORGANISM: Artificial Sequence
<220> FEATURE:
<223> OTHER INFORMATION: Synthesized

<400> SEQUENCE: 73
gctgtagcgt agtg                                                        14

<210> SEQ ID NO 74
<211> LENGTH: 14
<212> TYPE: DNA
<213> ORGANISM: Artificial Sequence
<220> FEATURE:
<223> OTHER INFORMATION: Synthesized

<400> SEQUENCE: 74
tctgtgcgtg tact                                                        14

<210> SEQ ID NO 75
<211> LENGTH: 14
<212> TYPE: DNA
<213> ORGANISM: Artificial Sequence
<220> FEATURE:
<223> OTHER INFORMATION: Synthesized

<400> SEQUENCE: 75
gagatatcgt gata                                                        14

<210> SEQ ID NO 76
<211> LENGTH: 14
<212> TYPE: DNA
<213> ORGANISM: Artificial Sequence
<220> FEATURE:
<223> OTHER INFORMATION: Synthesized
```

```
<400> SEQUENCE: 76
tcgactagac agta                                                      14

<210> SEQ ID NO 77
<211> LENGTH: 14
<212> TYPE: DNA
<213> ORGANISM: Artificial Sequence
<220> FEATURE:
<223> OTHER INFORMATION: Synthesized

<400> SEQUENCE: 77
gcgacatatc agtg                                                      14

<210> SEQ ID NO 78
<211> LENGTH: 14
<212> TYPE: DNA
<213> ORGANISM: Artificial Sequence
<220> FEATURE:
<223> OTHER INFORMATION: Synthesized

<400> SEQUENCE: 78
cgcactatgt agta                                                      14

<210> SEQ ID NO 79
<211> LENGTH: 14
<212> TYPE: DNA
<213> ORGANISM: Artificial Sequence
<220> FEATURE:
<223> OTHER INFORMATION: Synthesized

<400> SEQUENCE: 79
agcgacgaca gcgt                                                      14

<210> SEQ ID NO 80
<211> LENGTH: 14
<212> TYPE: DNA
<213> ORGANISM: Artificial Sequence
<220> FEATURE:
<223> OTHER INFORMATION: Synthesized

<400> SEQUENCE: 80
ctcatatcgt gcgc                                                      14

<210> SEQ ID NO 81
<211> LENGTH: 14
<212> TYPE: DNA
<213> ORGANISM: Artificial Sequence
<220> FEATURE:
<223> OTHER INFORMATION: Synthesized

<400> SEQUENCE: 81
gagactatga gatg                                                      14

<210> SEQ ID NO 82
<211> LENGTH: 14
<212> TYPE: DNA
<213> ORGANISM: Artificial Sequence
<220> FEATURE:
<223> OTHER INFORMATION: Synthesized

<400> SEQUENCE: 82
gctcgctacg tcag                                                      14

<210> SEQ ID NO 83
<211> LENGTH: 14
```

```
<212> TYPE: DNA
<213> ORGANISM: Artificial Sequence
<220> FEATURE:
<223> OTHER INFORMATION: Synthesized

<400> SEQUENCE: 83
cgcactcgtg ctca                                                        14

<210> SEQ ID NO 84
<211> LENGTH: 14
<212> TYPE: DNA
<213> ORGANISM: Artificial Sequence
<220> FEATURE:
<223> OTHER INFORMATION: Synthesized

<400> SEQUENCE: 84
gcgtgctaca gaca                                                        14

<210> SEQ ID NO 85
<211> LENGTH: 14
<212> TYPE: DNA
<213> ORGANISM: Artificial Sequence
<220> FEATURE:
<223> OTHER INFORMATION: Synthesized

<400> SEQUENCE: 85
agcatgctca cgac                                                        14

<210> SEQ ID NO 86
<211> LENGTH: 14
<212> TYPE: DNA
<213> ORGANISM: Artificial Sequence
<220> FEATURE:
<223> OTHER INFORMATION: Synthesized

<400> SEQUENCE: 86
tcgtcagaca cgac                                                        14

<210> SEQ ID NO 87
<211> LENGTH: 14
<212> TYPE: DNA
<213> ORGANISM: Artificial Sequence
<220> FEATURE:
<223> OTHER INFORMATION: Synthesized

<400> SEQUENCE: 87
agcgtagcat agac                                                        14

<210> SEQ ID NO 88
<211> LENGTH: 14
<212> TYPE: DNA
<213> ORGANISM: Artificial Sequence
<220> FEATURE:
<223> OTHER INFORMATION: Synthesized

<400> SEQUENCE: 88
tatcagagat gcgt                                                        14

<210> SEQ ID NO 89
<211> LENGTH: 14
<212> TYPE: DNA
<213> ORGANISM: Artificial Sequence
<220> FEATURE:
<223> OTHER INFORMATION: Synthesized

<400> SEQUENCE: 89
```

```
tcgtctatcg tcgt                                                         14

<210> SEQ ID NO 90
<211> LENGTH: 14
<212> TYPE: DNA
<213> ORGANISM: Artificial Sequence
<220> FEATURE:
<223> OTHER INFORMATION: Synthesized

<400> SEQUENCE: 90
ctcgacgaca cgta                                                         14

<210> SEQ ID NO 91
<211> LENGTH: 14
<212> TYPE: DNA
<213> ORGANISM: Artificial Sequence
<220> FEATURE:
<223> OTHER INFORMATION: Synthesized

<400> SEQUENCE: 91
agacacgacg ctca                                                         14

<210> SEQ ID NO 92
<211> LENGTH: 14
<212> TYPE: DNA
<213> ORGANISM: Artificial Sequence
<220> FEATURE:
<223> OTHER INFORMATION: Synthesized

<400> SEQUENCE: 92
ctatctcgtc tcac                                                         14

<210> SEQ ID NO 93
<211> LENGTH: 14
<212> TYPE: DNA
<213> ORGANISM: Artificial Sequence
<220> FEATURE:
<223> OTHER INFORMATION: Synthesized

<400> SEQUENCE: 93
tctcactatc atgc                                                         14

<210> SEQ ID NO 94
<211> LENGTH: 14
<212> TYPE: DNA
<213> ORGANISM: Artificial Sequence
<220> FEATURE:
<223> OTHER INFORMATION: Synthesized

<400> SEQUENCE: 94
gctgagatca cgac                                                         14

<210> SEQ ID NO 95
<211> LENGTH: 14
<212> TYPE: DNA
<213> ORGANISM: Artificial Sequence
<220> FEATURE:
<223> OTHER INFORMATION: Synthesized

<400> SEQUENCE: 95
atatgcgatc atct                                                         14

<210> SEQ ID NO 96
<211> LENGTH: 14
<212> TYPE: DNA
<213> ORGANISM: Artificial Sequence
```

```
<220> FEATURE:
<223> OTHER INFORMATION: Synthesized

<400> SEQUENCE: 96
gcgtgctcat atct                                                14

<210> SEQ ID NO 97
<211> LENGTH: 14
<212> TYPE: DNA
<213> ORGANISM: Artificial Sequence
<220> FEATURE:
<223> OTHER INFORMATION: Synthesized

<400> SEQUENCE: 97
tctcgtatcg cgtg                                                14

<210> SEQ ID NO 98
<211> LENGTH: 14
<212> TYPE: DNA
<213> ORGANISM: Artificial Sequence
<220> FEATURE:
<223> OTHER INFORMATION: Synthesized

<400> SEQUENCE: 98
agatctctgt gaca                                                14

<210> SEQ ID NO 99
<211> LENGTH: 14
<212> TYPE: DNA
<213> ORGANISM: Artificial Sequence
<220> FEATURE:
<223> OTHER INFORMATION: Synthesized

<400> SEQUENCE: 99
gagatatacg cgag                                                14

<210> SEQ ID NO 100
<211> LENGTH: 14
<212> TYPE: DNA
<213> ORGANISM: Artificial Sequence
<220> FEATURE:
<223> OTHER INFORMATION: Synthesized

<400> SEQUENCE: 100
atcgtgagat gatg                                                14

<210> SEQ ID NO 101
<211> LENGTH: 14
<212> TYPE: DNA
<213> ORGANISM: Artificial Sequence
<220> FEATURE:
<223> OTHER INFORMATION: Synthesized

<400> SEQUENCE: 101
tctcacgcac tatg                                                14

<210> SEQ ID NO 102
<211> LENGTH: 14
<212> TYPE: DNA
<213> ORGANISM: Artificial Sequence
<220> FEATURE:
<223> OTHER INFORMATION: Synthesized

<400> SEQUENCE: 102
gcgatgcgtg tcac                                                14
```

```
<210> SEQ ID NO 103
<211> LENGTH: 14
<212> TYPE: DNA
<213> ORGANISM: Artificial Sequence
<220> FEATURE:
<223> OTHER INFORMATION: Synthesized

<400> SEQUENCE: 103
tcgtgtcgat agag                                                        14

<210> SEQ ID NO 104
<211> LENGTH: 14
<212> TYPE: DNA
<213> ORGANISM: Artificial Sequence
<220> FEATURE:
<223> OTHER INFORMATION: Synthesized

<400> SEQUENCE: 104
gatcactatg cgta                                                        14

<210> SEQ ID NO 105
<211> LENGTH: 14
<212> TYPE: DNA
<213> ORGANISM: Artificial Sequence
<220> FEATURE:
<223> OTHER INFORMATION: Synthesized

<400> SEQUENCE: 105
ctacgtagtc tata                                                        14

<210> SEQ ID NO 106
<211> LENGTH: 14
<212> TYPE: DNA
<213> ORGANISM: Artificial Sequence
<220> FEATURE:
<223> OTHER INFORMATION: Synthesized

<400> SEQUENCE: 106
gagtgcgcac tcgt                                                        14

<210> SEQ ID NO 107
<211> LENGTH: 14
<212> TYPE: DNA
<213> ORGANISM: Artificial Sequence
<220> FEATURE:
<223> OTHER INFORMATION: Synthesized

<400> SEQUENCE: 107
tcgtgctatg tatg                                                        14

<210> SEQ ID NO 108
<211> LENGTH: 14
<212> TYPE: DNA
<213> ORGANISM: Artificial Sequence
<220> FEATURE:
<223> OTHER INFORMATION: Synthesized

<400> SEQUENCE: 108
agatgtagac tact                                                        14

<210> SEQ ID NO 109
<211> LENGTH: 14
<212> TYPE: DNA
<213> ORGANISM: Artificial Sequence
<220> FEATURE:
<223> OTHER INFORMATION: Synthesized
```

```
<400> SEQUENCE: 109
atacagagat atgc                                                        14

<210> SEQ ID NO 110
<211> LENGTH: 14
<212> TYPE: DNA
<213> ORGANISM: Artificial Sequence
<220> FEATURE:
<223> OTHER INFORMATION: Synthesized

<400> SEQUENCE: 110
ctacagctcg tata                                                        14

<210> SEQ ID NO 111
<211> LENGTH: 14
<212> TYPE: DNA
<213> ORGANISM: Artificial Sequence
<220> FEATURE:
<223> OTHER INFORMATION: Synthesized

<400> SEQUENCE: 111
cgacgtctga gatg                                                        14

<210> SEQ ID NO 112
<211> LENGTH: 14
<212> TYPE: DNA
<213> ORGANISM: Artificial Sequence
<220> FEATURE:
<223> OTHER INFORMATION: Synthesized

<400> SEQUENCE: 112
ctcgagcgat gcgc                                                        14

<210> SEQ ID NO 113
<211> LENGTH: 14
<212> TYPE: DNA
<213> ORGANISM: Artificial Sequence
<220> FEATURE:
<223> OTHER INFORMATION: Synthesized

<400> SEQUENCE: 113
tagatagatc atca                                                        14

<210> SEQ ID NO 114
<211> LENGTH: 14
<212> TYPE: DNA
<213> ORGANISM: Artificial Sequence
<220> FEATURE:
<223> OTHER INFORMATION: Synthesized

<400> SEQUENCE: 114
agcatgcgac taca                                                        14

<210> SEQ ID NO 115
<211> LENGTH: 14
<212> TYPE: DNA
<213> ORGANISM: Artificial Sequence
<220> FEATURE:
<223> OTHER INFORMATION: Synthesized

<400> SEQUENCE: 115
cgcgagctga ctca                                                        14

<210> SEQ ID NO 116
```

```
<211> LENGTH: 14
<212> TYPE: DNA
<213> ORGANISM: Artificial Sequence
<220> FEATURE:
<223> OTHER INFORMATION: Synthesized

<400> SEQUENCE: 116
gatgtagacg tcgc                                                     14

<210> SEQ ID NO 117
<211> LENGTH: 14
<212> TYPE: DNA
<213> ORGANISM: Artificial Sequence
<220> FEATURE:
<223> OTHER INFORMATION: Synthesized

<400> SEQUENCE: 117
cgcatgatca gatg                                                     14

<210> SEQ ID NO 118
<211> LENGTH: 14
<212> TYPE: DNA
<213> ORGANISM: Artificial Sequence
<220> FEATURE:
<223> OTHER INFORMATION: Synthesized

<400> SEQUENCE: 118
gcgtcatcga gcgc                                                     14

<210> SEQ ID NO 119
<211> LENGTH: 14
<212> TYPE: DNA
<213> ORGANISM: Artificial Sequence
<220> FEATURE:
<223> OTHER INFORMATION: Synthesized

<400> SEQUENCE: 119
ctacagcgtc atct                                                     14

<210> SEQ ID NO 120
<211> LENGTH: 14
<212> TYPE: DNA
<213> ORGANISM: Artificial Sequence
<220> FEATURE:
<223> OTHER INFORMATION: Synthesized

<400> SEQUENCE: 120
atacgcgcac tcac                                                     14

<210> SEQ ID NO 121
<211> LENGTH: 14
<212> TYPE: DNA
<213> ORGANISM: Artificial Sequence
<220> FEATURE:
<223> OTHER INFORMATION: Synthesized

<400> SEQUENCE: 121
ctatgtatga gcac                                                     14

<210> SEQ ID NO 122
<211> LENGTH: 14
<212> TYPE: DNA
<213> ORGANISM: Artificial Sequence
<220> FEATURE:
<223> OTHER INFORMATION: Synthesized

<400> SEQUENCE: 122
```

```
ctcgtgatga cgag                                                         14

<210> SEQ ID NO 123
<211> LENGTH: 14
<212> TYPE: DNA
<213> ORGANISM: Artificial Sequence
<220> FEATURE:
<223> OTHER INFORMATION: Synthesized

<400> SEQUENCE: 123
cgcgacgcac atgc                                                         14

<210> SEQ ID NO 124
<211> LENGTH: 14
<212> TYPE: DNA
<213> ORGANISM: Artificial Sequence
<220> FEATURE:
<223> OTHER INFORMATION: Synthesized

<400> SEQUENCE: 124
ctatcagacg tcag                                                         14

<210> SEQ ID NO 125
<211> LENGTH: 14
<212> TYPE: DNA
<213> ORGANISM: Artificial Sequence
<220> FEATURE:
<223> OTHER INFORMATION: Synthesized

<400> SEQUENCE: 125
atacagagtg cgag                                                         14

<210> SEQ ID NO 126
<211> LENGTH: 14
<212> TYPE: DNA
<213> ORGANISM: Artificial Sequence
<220> FEATURE:
<223> OTHER INFORMATION: Synthesized

<400> SEQUENCE: 126
atacgtatca ctgc                                                         14

<210> SEQ ID NO 127
<211> LENGTH: 14
<212> TYPE: DNA
<213> ORGANISM: Artificial Sequence
<220> FEATURE:
<223> OTHER INFORMATION: Synthesized

<400> SEQUENCE: 127
cgacagctca gcac                                                         14

<210> SEQ ID NO 128
<211> LENGTH: 14
<212> TYPE: DNA
<213> ORGANISM: Artificial Sequence
<220> FEATURE:
<223> OTHER INFORMATION: Synthesized

<400> SEQUENCE: 128
ctatcagcga gatg                                                         14

<210> SEQ ID NO 129
<211> LENGTH: 14
<212> TYPE: DNA
```

```
<213> ORGANISM: Artificial Sequence
<220> FEATURE:
<223> OTHER INFORMATION: Synthesized

<400> SEQUENCE: 129
atcactcgat agtg                                                         14

<210> SEQ ID NO 130
<211> LENGTH: 14
<212> TYPE: DNA
<213> ORGANISM: Artificial Sequence
<220> FEATURE:
<223> OTHER INFORMATION: Synthesized

<400> SEQUENCE: 130
cgcatatcat atct                                                         14

<210> SEQ ID NO 131
<211> LENGTH: 14
<212> TYPE: DNA
<213> ORGANISM: Artificial Sequence
<220> FEATURE:
<223> OTHER INFORMATION: Synthesized

<400> SEQUENCE: 131
cgcgagagtg taca                                                         14

<210> SEQ ID NO 132
<211> LENGTH: 14
<212> TYPE: DNA
<213> ORGANISM: Artificial Sequence
<220> FEATURE:
<223> OTHER INFORMATION: Synthesized

<400> SEQUENCE: 132
gagatgctga gcgc                                                         14

<210> SEQ ID NO 133
<211> LENGTH: 14
<212> TYPE: DNA
<213> ORGANISM: Artificial Sequence
<220> FEATURE:
<223> OTHER INFORMATION: Synthesized

<400> SEQUENCE: 133
agcatgagtg ctgt                                                         14

<210> SEQ ID NO 134
<211> LENGTH: 14
<212> TYPE: DNA
<213> ORGANISM: Artificial Sequence
<220> FEATURE:
<223> OTHER INFORMATION: Synthesized

<400> SEQUENCE: 134
cgcgtagcga gcag                                                         14

<210> SEQ ID NO 135
<211> LENGTH: 14
<212> TYPE: DNA
<213> ORGANISM: Artificial Sequence
<220> FEATURE:
<223> OTHER INFORMATION: Synthesized

<400> SEQUENCE: 135
agatcatcat gcac                                                         14
```

```
<210> SEQ ID NO 136
<211> LENGTH: 14
<212> TYPE: DNA
<213> ORGANISM: Artificial Sequence
<220> FEATURE:
<223> OTHER INFORMATION: Synthesized

<400> SEQUENCE: 136
tctgtataca cgta                                                       14

<210> SEQ ID NO 137
<211> LENGTH: 14
<212> TYPE: DNA
<213> ORGANISM: Artificial Sequence
<220> FEATURE:
<223> OTHER INFORMATION: Synthesized

<400> SEQUENCE: 137
tctgtatcat gaca                                                       14

<210> SEQ ID NO 138
<211> LENGTH: 14
<212> TYPE: DNA
<213> ORGANISM: Artificial Sequence
<220> FEATURE:
<223> OTHER INFORMATION: Synthesized

<400> SEQUENCE: 138
tcgtctctca gata                                                       14

<210> SEQ ID NO 139
<211> LENGTH: 14
<212> TYPE: DNA
<213> ORGANISM: Artificial Sequence
<220> FEATURE:
<223> OTHER INFORMATION: Synthesized

<400> SEQUENCE: 139
atacacgatg tatg                                                       14

<210> SEQ ID NO 140
<211> LENGTH: 14
<212> TYPE: DNA
<213> ORGANISM: Artificial Sequence
<220> FEATURE:
<223> OTHER INFORMATION: Synthesized

<400> SEQUENCE: 140
atacgctcga ctca                                                       14

<210> SEQ ID NO 141
<211> LENGTH: 14
<212> TYPE: DNA
<213> ORGANISM: Artificial Sequence
<220> FEATURE:
<223> OTHER INFORMATION: Synthesized

<400> SEQUENCE: 141
tctgacgatg cgag                                                       14

<210> SEQ ID NO 142
<211> LENGTH: 14
<212> TYPE: DNA
<213> ORGANISM: Artificial Sequence
<220> FEATURE:
```

<223> OTHER INFORMATION: Synthesized

<400> SEQUENCE: 142
gatgagcgtc agag                                                          14

<210> SEQ ID NO 143
<211> LENGTH: 14
<212> TYPE: DNA
<213> ORGANISM: Artificial Sequence
<220> FEATURE:
<223> OTHER INFORMATION: Synthesized

<400> SEQUENCE: 143
gagtctcgtc atct                                                          14

<210> SEQ ID NO 144
<211> LENGTH: 14
<212> TYPE: DNA
<213> ORGANISM: Artificial Sequence
<220> FEATURE:
<223> OTHER INFORMATION: Synthesized

<400> SEQUENCE: 144
atacgtagat gcag                                                          14

<210> SEQ ID NO 145
<211> LENGTH: 14
<212> TYPE: DNA
<213> ORGANISM: Artificial Sequence
<220> FEATURE:
<223> OTHER INFORMATION: Synthesized

<400> SEQUENCE: 145
gatcacgatc tcac                                                          14

<210> SEQ ID NO 146
<211> LENGTH: 14
<212> TYPE: DNA
<213> ORGANISM: Artificial Sequence
<220> FEATURE:
<223> OTHER INFORMATION: Synthesized

<400> SEQUENCE: 146
atcactagtc atgc                                                          14

<210> SEQ ID NO 147
<211> LENGTH: 14
<212> TYPE: DNA
<213> ORGANISM: Artificial Sequence
<220> FEATURE:
<223> OTHER INFORMATION: Synthesized

<400> SEQUENCE: 147
tagtgcgcgt gatg                                                          14

<210> SEQ ID NO 148
<211> LENGTH: 14
<212> TYPE: DNA
<213> ORGANISM: Artificial Sequence
<220> FEATURE:
<223> OTHER INFORMATION: Synthesized

<400> SEQUENCE: 148
gctcagatcg tact                                                          14

```
<210> SEQ ID NO 149
<211> LENGTH: 14
<212> TYPE: DNA
<213> ORGANISM: Artificial Sequence
<220> FEATURE:
<223> OTHER INFORMATION: Synthesized

<400> SEQUENCE: 149
gctgactaca ctct                                                       14

<210> SEQ ID NO 150
<211> LENGTH: 14
<212> TYPE: DNA
<213> ORGANISM: Artificial Sequence
<220> FEATURE:
<223> OTHER INFORMATION: Synthesized

<400> SEQUENCE: 150
agcgagagac atct                                                       14

<210> SEQ ID NO 151
<211> LENGTH: 14
<212> TYPE: DNA
<213> ORGANISM: Artificial Sequence
<220> FEATURE:
<223> OTHER INFORMATION: Synthesized

<400> SEQUENCE: 151
tctcgtctga ctct                                                       14

<210> SEQ ID NO 152
<211> LENGTH: 14
<212> TYPE: DNA
<213> ORGANISM: Artificial Sequence
<220> FEATURE:
<223> OTHER INFORMATION: Synthesized

<400> SEQUENCE: 152
gatgacgcac agta                                                       14

<210> SEQ ID NO 153
<211> LENGTH: 14
<212> TYPE: DNA
<213> ORGANISM: Artificial Sequence
<220> FEATURE:
<223> OTHER INFORMATION: Synthesized

<400> SEQUENCE: 153
atcacagatg cgac                                                       14

<210> SEQ ID NO 154
<211> LENGTH: 14
<212> TYPE: DNA
<213> ORGANISM: Artificial Sequence
<220> FEATURE:
<223> OTHER INFORMATION: Synthesized

<400> SEQUENCE: 154
gcgactctcg ctgc                                                       14

<210> SEQ ID NO 155
<211> LENGTH: 14
<212> TYPE: DNA
<213> ORGANISM: Artificial Sequence
<220> FEATURE:
<223> OTHER INFORMATION: Synthesized
```

```
<400> SEQUENCE: 155
cgacagcgat gaca                                                    14

<210> SEQ ID NO 156
<211> LENGTH: 14
<212> TYPE: DNA
<213> ORGANISM: Artificial Sequence
<220> FEATURE:
<223> OTHER INFORMATION: Synthesized

<400> SEQUENCE: 156
agatcagcac atca                                                    14

<210> SEQ ID NO 157
<211> LENGTH: 14
<212> TYPE: DNA
<213> ORGANISM: Artificial Sequence
<220> FEATURE:
<223> OTHER INFORMATION: Synthesized

<400> SEQUENCE: 157
gctgtgagat gcac                                                    14

<210> SEQ ID NO 158
<211> LENGTH: 14
<212> TYPE: DNA
<213> ORGANISM: Artificial Sequence
<220> FEATURE:
<223> OTHER INFORMATION: Synthesized

<400> SEQUENCE: 158
gcgatagcat gcag                                                    14

<210> SEQ ID NO 159
<211> LENGTH: 14
<212> TYPE: DNA
<213> ORGANISM: Artificial Sequence
<220> FEATURE:
<223> OTHER INFORMATION: Synthesized

<400> SEQUENCE: 159
gatcgtagtg cgac                                                    14

<210> SEQ ID NO 160
<211> LENGTH: 14
<212> TYPE: DNA
<213> ORGANISM: Artificial Sequence
<220> FEATURE:
<223> OTHER INFORMATION: Synthesized

<400> SEQUENCE: 160
ctcacatacg ctct                                                    14

<210> SEQ ID NO 161
<211> LENGTH: 14
<212> TYPE: DNA
<213> ORGANISM: Artificial Sequence
<220> FEATURE:
<223> OTHER INFORMATION: Synthesized

<400> SEQUENCE: 161
cgatgtcgat atgt                                                    14

<210> SEQ ID NO 162
<211> LENGTH: 14
```

```
<212> TYPE: DNA
<213> ORGANISM: Artificial Sequence
<220> FEATURE:
<223> OTHER INFORMATION: Synthesized

<400> SEQUENCE: 162
atcactatga ctct                                                      14

<210> SEQ ID NO 163
<211> LENGTH: 14
<212> TYPE: DNA
<213> ORGANISM: Artificial Sequence
<220> FEATURE:
<223> OTHER INFORMATION: Synthesized

<400> SEQUENCE: 163
tcgatagcgt atgt                                                      14

<210> SEQ ID NO 164
<211> LENGTH: 14
<212> TYPE: DNA
<213> ORGANISM: Artificial Sequence
<220> FEATURE:
<223> OTHER INFORMATION: Synthesized

<400> SEQUENCE: 164
atacactcgt agag                                                      14

<210> SEQ ID NO 165
<211> LENGTH: 14
<212> TYPE: DNA
<213> ORGANISM: Artificial Sequence
<220> FEATURE:
<223> OTHER INFORMATION: Synthesized

<400> SEQUENCE: 165
gcgtgtatgt gact                                                      14

<210> SEQ ID NO 166
<211> LENGTH: 14
<212> TYPE: DNA
<213> ORGANISM: Artificial Sequence
<220> FEATURE:
<223> OTHER INFORMATION: Synthesized

<400> SEQUENCE: 166
tatcagatga cgta                                                      14

<210> SEQ ID NO 167
<211> LENGTH: 14
<212> TYPE: DNA
<213> ORGANISM: Artificial Sequence
<220> FEATURE:
<223> OTHER INFORMATION: Synthesized

<400> SEQUENCE: 167
gagactctgt agac                                                      14

<210> SEQ ID NO 168
<211> LENGTH: 14
<212> TYPE: DNA
<213> ORGANISM: Artificial Sequence
<220> FEATURE:
<223> OTHER INFORMATION: Synthesized

<400> SEQUENCE: 168
```

```
gcgtgcgcga cgta                                                      14

<210> SEQ ID NO 169
<211> LENGTH: 14
<212> TYPE: DNA
<213> ORGANISM: Artificial Sequence
<220> FEATURE:
<223> OTHER INFORMATION: Synthesized

<400> SEQUENCE: 169
tagtcagatc tcgc                                                      14

<210> SEQ ID NO 170
<211> LENGTH: 14
<212> TYPE: DNA
<213> ORGANISM: Artificial Sequence
<220> FEATURE:
<223> OTHER INFORMATION: Synthesized

<400> SEQUENCE: 170
agacagcgac tcgt                                                      14

<210> SEQ ID NO 171
<211> LENGTH: 14
<212> TYPE: DNA
<213> ORGANISM: Artificial Sequence
<220> FEATURE:
<223> OTHER INFORMATION: Synthesized

<400> SEQUENCE: 171
cgatcagatc agac                                                      14

<210> SEQ ID NO 172
<211> LENGTH: 14
<212> TYPE: DNA
<213> ORGANISM: Artificial Sequence
<220> FEATURE:
<223> OTHER INFORMATION: Synthesized

<400> SEQUENCE: 172
gatgacgaca gatg                                                      14

<210> SEQ ID NO 173
<211> LENGTH: 14
<212> TYPE: DNA
<213> ORGANISM: Artificial Sequence
<220> FEATURE:
<223> OTHER INFORMATION: Synthesized

<400> SEQUENCE: 173
agcgagatgt gcac                                                      14

<210> SEQ ID NO 174
<211> LENGTH: 14
<212> TYPE: DNA
<213> ORGANISM: Artificial Sequence
<220> FEATURE:
<223> OTHER INFORMATION: Synthesized

<400> SEQUENCE: 174
gcgtcagcac tata                                                      14

<210> SEQ ID NO 175
<211> LENGTH: 14
<212> TYPE: DNA
<213> ORGANISM: Artificial Sequence
```

```
<220> FEATURE:
<223> OTHER INFORMATION: Synthesized

<400> SEQUENCE: 175
agcgtataca ctgc                                                         14

<210> SEQ ID NO 176
<211> LENGTH: 14
<212> TYPE: DNA
<213> ORGANISM: Artificial Sequence
<220> FEATURE:
<223> OTHER INFORMATION: Synthesized

<400> SEQUENCE: 176
ctcatgctgt gact                                                         14

<210> SEQ ID NO 177
<211> LENGTH: 14
<212> TYPE: DNA
<213> ORGANISM: Artificial Sequence
<220> FEATURE:
<223> OTHER INFORMATION: Synthesized

<400> SEQUENCE: 177
gagatgatcg tata                                                         14

<210> SEQ ID NO 178
<211> LENGTH: 14
<212> TYPE: DNA
<213> ORGANISM: Artificial Sequence
<220> FEATURE:
<223> OTHER INFORMATION: Synthesized

<400> SEQUENCE: 178
tatgactatc tact                                                         14

<210> SEQ ID NO 179
<211> LENGTH: 14
<212> TYPE: DNA
<213> ORGANISM: Artificial Sequence
<220> FEATURE:
<223> OTHER INFORMATION: Synthesized

<400> SEQUENCE: 179
tagatgatgt agtg                                                         14

<210> SEQ ID NO 180
<211> LENGTH: 14
<212> TYPE: DNA
<213> ORGANISM: Artificial Sequence
<220> FEATURE:
<223> OTHER INFORMATION: Synthesized

<400> SEQUENCE: 180
tcgacatcac tcgt                                                         14

<210> SEQ ID NO 181
<211> LENGTH: 14
<212> TYPE: DNA
<213> ORGANISM: Artificial Sequence
<220> FEATURE:
<223> OTHER INFORMATION: Synthesized

<400> SEQUENCE: 181
gctgactcac tcgc                                                         14
```

<210> SEQ ID NO 182
<211> LENGTH: 14
<212> TYPE: DNA
<213> ORGANISM: Artificial Sequence
<220> FEATURE:
<223> OTHER INFORMATION: Synthesized

<400> SEQUENCE: 182
gagtgtctcg tcac                                                     14

<210> SEQ ID NO 183
<211> LENGTH: 14
<212> TYPE: DNA
<213> ORGANISM: Artificial Sequence
<220> FEATURE:
<223> OTHER INFORMATION: Synthesized

<400> SEQUENCE: 183
cgacactcga gcgt                                                     14

<210> SEQ ID NO 184
<211> LENGTH: 14
<212> TYPE: DNA
<213> ORGANISM: Artificial Sequence
<220> FEATURE:
<223> OTHER INFORMATION: Synthesized

<400> SEQUENCE: 184
tatcacgcga ctgc                                                     14

<210> SEQ ID NO 185
<211> LENGTH: 14
<212> TYPE: DNA
<213> ORGANISM: Artificial Sequence
<220> FEATURE:
<223> OTHER INFORMATION: Synthesized

<400> SEQUENCE: 185
agatgtatgt agag                                                     14

<210> SEQ ID NO 186
<211> LENGTH: 14
<212> TYPE: DNA
<213> ORGANISM: Artificial Sequence
<220> FEATURE:
<223> OTHER INFORMATION: Synthesized

<400> SEQUENCE: 186
agacgtcgac agac                                                     14

<210> SEQ ID NO 187
<211> LENGTH: 14
<212> TYPE: DNA
<213> ORGANISM: Artificial Sequence
<220> FEATURE:
<223> OTHER INFORMATION: Synthesized

<400> SEQUENCE: 187
atcgagctcg tcag                                                     14

<210> SEQ ID NO 188
<211> LENGTH: 14
<212> TYPE: DNA
<213> ORGANISM: Artificial Sequence
<220> FEATURE:
<223> OTHER INFORMATION: Synthesized

```
<400> SEQUENCE: 188
tctgagatgt atgc                                                        14

<210> SEQ ID NO 189
<211> LENGTH: 14
<212> TYPE: DNA
<213> ORGANISM: Artificial Sequence
<220> FEATURE:
<223> OTHER INFORMATION: Synthesized

<400> SEQUENCE: 189
agcgactcga cgac                                                        14

<210> SEQ ID NO 190
<211> LENGTH: 14
<212> TYPE: DNA
<213> ORGANISM: Artificial Sequence
<220> FEATURE:
<223> OTHER INFORMATION: Synthesized

<400> SEQUENCE: 190
gagacatatg tact                                                        14

<210> SEQ ID NO 191
<211> LENGTH: 14
<212> TYPE: DNA
<213> ORGANISM: Artificial Sequence
<220> FEATURE:
<223> OTHER INFORMATION: Synthesized

<400> SEQUENCE: 191
gctgtgagtg cgtg                                                        14

<210> SEQ ID NO 192
<211> LENGTH: 14
<212> TYPE: DNA
<213> ORGANISM: Artificial Sequence
<220> FEATURE:
<223> OTHER INFORMATION: Synthesized

<400> SEQUENCE: 192
ctcatgcgtc tcgt                                                        14

<210> SEQ ID NO 193
<211> LENGTH: 14
<212> TYPE: DNA
<213> ORGANISM: Artificial Sequence
<220> FEATURE:
<223> OTHER INFORMATION: Synthesized

<400> SEQUENCE: 193
tatgactcgt gcac                                                        14

<210> SEQ ID NO 194
<211> LENGTH: 14
<212> TYPE: DNA
<213> ORGANISM: Artificial Sequence
<220> FEATURE:
<223> OTHER INFORMATION: Synthesized

<400> SEQUENCE: 194
agacgctcac atgt                                                        14

<210> SEQ ID NO 195
```

```
<211> LENGTH: 14
<212> TYPE: DNA
<213> ORGANISM: Artificial Sequence
<220> FEATURE:
<223> OTHER INFORMATION: Synthesized

<400> SEQUENCE: 195
cgcgtagatg cgtg                                                14

<210> SEQ ID NO 196
<211> LENGTH: 14
<212> TYPE: DNA
<213> ORGANISM: Artificial Sequence
<220> FEATURE:
<223> OTHER INFORMATION: Synthesized

<400> SEQUENCE: 196
ctacacgaca gact                                                14

<210> SEQ ID NO 197
<211> LENGTH: 14
<212> TYPE: DNA
<213> ORGANISM: Artificial Sequence
<220> FEATURE:
<223> OTHER INFORMATION: Synthesized

<400> SEQUENCE: 197
cgatgtcgtg cgag                                                14

<210> SEQ ID NO 198
<211> LENGTH: 14
<212> TYPE: DNA
<213> ORGANISM: Artificial Sequence
<220> FEATURE:
<223> OTHER INFORMATION: Synthesized

<400> SEQUENCE: 198
tagatgcgac agac                                                14
```

METHOD FOR THE DECONVOLUTION OF NUCLEIC ACID-CONTAINING SUBSTANCE MIXTURES

The invention relates to a method for the deconvolution of substance mixtures comprising nucleic acid, using synthetically generated target nucleotide sequences.

Nucleic acids serve in nature for coding genetic information. Methods for detecting and interpreting nucleotide sequences—from which nucleic acids are formed—are therefore of great interest for many fields of research. With methods according to Maxam and Gilbert or according to Sanger, pioneering foundation stones for sequencing of nucleic acids could be laid. Also methods for synthesis of short nucleotide sequences (oligonucleotide synthesis), such as for example the phosphite triester method, have already been established and are part of the state of the art. Because of these capabilities, further methods have been developed which make nucleotide sequences, in particular DNA sequences, usable as information carriers. A technology which uses DNA molecules for storing information is termed DNA barcoding. It is the aim thereby to synthesise short DNA sequences—the so-called DNA barcodes—in order then to assign them to known (normally larger) nucleotide sequences or substances, or to couple them with the nucleotide sequence or substance which represents them. Identification of nucleotide sequences or substances prepared in this way is then possible in a simple manner using the respective DNA barcode, the short sequences of which can be sequenced in a short time and/or amplified with corresponding methods (PGR) and consequently can be enriched. Because of the ability of nucleotide sequences to be amplified, methods based on nucleic acid count, in the field of analytical chemistry and biochemistry, as the most sensitive detection methods.

A further field of application resides in chemical, biological and medical research. A central object here resides in the discovery of molecular structures with specific binding affinities for proteins. For this purpose, DNA-coded chemical molecule libraries serve as effective tool for tracking down ligands for pharmaceutically relevant proteins. Thus DNA-coded molecules can be enriched for example by an affinity-based selection and subsequently be decoded on the basis of their unequivocal DNA coding (DNA barcode). Normally DNA-coded substance mixtures are obtained with such selection experiments (screenings). Such mixtures normally comprise a large number of DNA-coded substances.

Despite this, isolation- or purification steps are extensively dispensed with for reasons of cost in the analysis of substance mixtures from selection experiments. The thereby detected data are based expediently on the assumption that the DNA barcodes of enriched substances are present in such a mixture with a higher probability and consequently are also sequenced with increased probability. However, this correlation does not necessarily apply. Thus the result can be impaired by several factors, such as for example because of the transformation of different plasmids in bacteria (in preparation for Sanger sequencing) or by annealing—and amplification processes on micro/nanostructures (deep sequencing methods). This state of affairs makes necessary a further time-consuming method step in which it must be checked whether the supposedly identified substance actually concerns the substance enriched in the mixture.

With respect to the low parallelisation capacity of normal sequencing methods (Maxam and Gilbert or dideoxy method according to Sanger), a complex sample preparation is therefore unavoidable, in particular in the case of substance mixtures which have no significant enrichment of a sought nucleic acid or of a nucleotide sequence. Furthermore, also sequencing methods of the new generation, such as for example pyro-sequencing, require isolation and purification of a sample mixture before the actual sequencing can be began.

It is therefore intended to be the object of the invention to propose a method with which individual nucleotide sequences in substance mixtures comprising nucleic acid can be identified within a short time and economically.

This object is achieved by the method described and claimed below, with advantageous embodiments and developments of the method according to the invention also achieved with features described and claimed below.

According to the present invention, a method for the deconvolution of substance mixtures comprising nucleic acid is proposed for achieving the object, in the case of which, in a first step, a plurality of target nucleotide sequences (TNS) $(A_1-A_n, B_1-B_n, \ldots, Z_n)$, which differ from each other, with $N_0-N_n$ sequence positions, are generated from a plurality of nucleotides (A, C, G, T/U) according to a prescribed algorithm. In a further step, respectively at least one of the generated TNS $(A_1-A_n, B_1-B_n, \ldots, Z_n)$ is assigned to at least one substance or one substance combination and coupled chemically with the latter. Furthermore, in the case of the method according to the invention, at least one substance mixture to be analysed, with at least two different substances TNS and/or are TNS-coupled substances contained therein, is prepared, which at least one substance mixture is sequenced according to a sequencing method, all of the TNS $(A_1-A_n, B_1-B_n, \ldots, Z_n)$ or further nucleic acids or nucleotide sequences contained in the substance mixture being detected in a common sequence spectrum at the same time. In order to facilitate the deconvolution and hence to identify enriched TNS, the sequence spectra of a substance mixture should be withdrawn/subtracted from each other before and after a selection experiment.

Simultaneously or subsequently thereto, the sequences superimposed in the sequence spectrum are deconvoluted by scanning the sequence positions $N_0-N_n$ according to the prescribed algorithm and are identified according to their assignment as a substance or substance combination. For example, the process can thereby take place such that sequence positions $N_0-N_n$, which have a significantly increased signal intensity of individual nucleotides (A, C, G, T/U) in the sequence spectrum, are scanned according to the prescribed algorithm.

The intensity of a signal of a nucleotide (A, C, G, T/U) at a sequence position $N_0-N_n$ corresponds to the frequency of a nucleotide (A, C, G, T/U) at the observed sequence position $N_0-N_n$. The signal can preferably concern a light signal, such as for example externally excited fluorescence or chemiluminescence. Accordingly, the detection limit for defecting a nucleotide (A, C, G, T/U) is dependent upon background noise or upon the sensitivity of the method and/or detector used.

A signal intensity of a nucleotide (A, C, G, T/U) should be judged to be significant if it is increased at a sequence position $N_0-N_n$ relative to at least one nucleotide, preferably relative to two nucleotides, particularly preferably relative to three nucleotides, by at least 5%, preferably by at least 30%. At a sequence position $N_0-N_n$, also significantly increased signal intensities can thereby be present for two or three nucleotides (A, C, G, T/U).

The sequence spectrum absorbed during sequencing should illustrate at least $N_0-N_n$ sequence positions of TNS to be identified. It is particularly advantageous if a relative frequency of individual nucleotides (A, C, G, T/U) can be demonstrated at the respective sequence positions in the sequence spectrum. Such a frequency distribution can be determined by comparison of the signal intensities of the individual nucleotides at the respective sequence positions. Determination of the frequency can also be effected by means of at least one standard TNS which is supplied to the substance mixture to be analysed in a known concentration before the sequencing step is effected.

Thus, the deconvolution of the sequence spectrum can also be implemented additionally or alternatively, such that significantly increased signal intensities of individual nucleotides (A, C, G, T/U) in the sequence spectrum are subtracted step-wise until the smallest (readable) signal intensity is reached at every sequence position $N_0$-$N_n$ for at most one nucleotide (A, C, G, T/U), and the thereby obtained subtraction spectra, which have respectively at least one sequence or at least sequence portions, are scanned at the sequence positions $N_0$-$N_n$ according to the prescribed algorithm.

The essential advantage of the method according to the invention resides in the use of the prescribed algorithm, on the basis of which a large number of TNS with a high degree of differentiation can be generated. The high degree of differentiation has an advantageous effect, in particular on identification of individual TNS, which can be effected consequently with increased sensitivity. Thus the identity of a TNS or of a possible TNS candidate can be determined in fact by a small number of sequence positions of a nucleotide sequence scanned according to the prescribable algorithm. In this way, even sequence spectra with individual sequences or sequence fragments which are superimposed multiple times can be deconvoluted, in which preferably sequence positions $N_0$-$N_n$ can be scanned with the known sequence difference according to the prescribed algorithm. Deconvolution of a substance mixture comprising a nucleic acid can therefore be effected with respect to one TNS to be identified without amplification- or isolation steps.

Normally, the decoding is effected after performing selection experiments which are implemented by DNA arrays and high-throughput sequencing/deep sequencing/next-generation sequencing. This is expensive and complex. It is possible by means of the method according to the invention, after performing selection experiments, to deconvolute a mixture comprising a nucleic acid, such as for example a DNA mixture, quickly, economically and simply, for example by means of Sanger sequencing.

In the identification of enriched (similar) TNS, it suffices in fact, that merely those sequence positions of the sequence spectrum which have a significantly increased signal intensity for individual nucleotides (A, C, G, T/U) are scanned. The resolved TNS then serve as proof of the presence of the substance assigned respectively to them. There should be understood here by the term substance, preferably molecules, molecule components and in particular the functional and/or structural group thereof. In the case of the term substance, according to the type of application, it can also concern carbon black-, tobacco smoke-, smog-, oil fumes-, flue dust-, cement dust-, metal-, metal oxide-, plastic material-, pollen-, bacteria- or virus particles.

A nucleotide occupancy for nucleotides (A, C, G, T/U) at the sequence positions $N_0$-$N_n$ of a TNS ($A_1$-$A_n$, $B_1$-$B_n$, ..., $Z_n$) to be formed can be established by the prescribed algorithm. For this purpose, a condition can be prescribed for each sequence position $N_0$-$N_n$ which can be linked to a nucleotide occupancy of at least one further sequence position. Thus, in the formation of the TNS according to the algorithm, the process can take place for example such that, for each sequence position $N_{0+1}$-$N_n$ of a TNS to be formed, a restriction related to a nucleotide (A, C, G, T/U) of a preceding sequence position is prescribed for respectively at least one nucleotide (A, C, G, T/U).

For a preferably simple identification of the TNS, it is advantageous if the formed TNS differ from each other at at least two sequence positions and/or by at least one nucleotide sequence consisting of at least five sequence positions. Appropriately, TNS which have a sequence difference of at least 75%, preferably more than 80%, particularly preferably more than 90%, are assigned respectively to substances which have the greatest structural and/or functional difference relative to each other.

Preferably, the TNS which respectively represent individual substances are respectively of the same length, i.e. have respectively the same number of sequence positions $N_0$-$N_n$. Thus identification can be simplified in fact simply by restricting the deconvolution to a prescribed sequence length. This also enables direct comparison at the respective sequence positions $N_0$-$N_n$ of superimposed TNS. In this context, it is advantageous furthermore if all of the TNS have a common sequence portion, on the basis of which they can be identified as such. This sequence portion should be produced preferably in the start- or end region of a TNS.

Furthermore, the formed TNS can have at least one sequence portion which codes a substance group, substance size, geocoordinates of an exposure location or a date. Properties of substances can also be coded via the length of the TNS, i.e. via the number of sequence positions. Properties of substances can also be coded in the form of different primer binding sites. For example, a TNS can code a geocoordinate. A substance group can be coded with a further sequence portion which acts as primer binding site during the sequencing. Hence using different primers during the sequencing reaction, the sequence of the respective TNS and thus the geocoordinate can be determined. By means of the respective primer used during the sequencing, it is known which substrate group is observed/taken into account in this case. In the production of the sequence of the primer binding site, the previously described algorithm is not used. Instead, this sequence should be designed with reference to parameters which permit a successful primer binding/sequencing. This can be for example the G/C content, the primer length and the primer melting temperature.

Combined substances and in particular those substances which have been combined with each other as a result of a selection experiment or affinity experiment can be coupled chemically with correspondingly combined TNS ($A_1$-$A_n$, $B_1$-$B_n$, ..., $Z_n$). Appropriately, TNS ($A_1$-$A_n$, $B_1$-$B_n$, ..., $Z_n$) and/or sequence portions of TNS ($A_1$-$A_n$, $B_1$-$B_n$, ..., $Z_n$) can be combined with each other.

Because of the multiplicity of possible sequence combinations, the formation of the TNS can be simulated in silica according to the prescribed algorithm. The formed TNS can thereby be examined also with respect to possible collisions with already known nucleotide sequences. The chemical synthesis of the TNS can then be effected preferably according to the phosphite triester method, Since the number of possible sequence combinations depends upon the number of available sequence positions, TNS with sufficient length, i.e. sufficient number of sequence positions $N_0$-$N_n$, should be formed, Accordingly, TNS with a length of more than five sequence positions should be formed or synthesised.

The TNS can be single- or double stranded RNA- or DNA molecules, double-stranded DNA molecules being preferred. The chemical coupling of the TNS to the substances representing them can preferably be effected by covalent bonding.

In the course of the method according to the invention, at least one method step for selection of at least, one TNS ($A_1$-$A_n$, $B_1$-$B_n$, ..., $Z_n$) or at least one TNS-coupled substance can be provided. Thus a first selection step can be implemented for example after the formation/synthesis of the TNS in order to remove incorrect TNS. A further selection step can be effected after coupling the TNS to their assigned substances so that incorrectly coupled substances can be determined and hence the quality of the library can be evaluated. The process can thereby fake place respectively such that the component to be selected (substance or TNS) which is located in a liquid mobile phase is bound to a stationary phase in which corresponding binding partners or conjugates of the component to be selected are immobilised. Thus respectively a substance mixture to be analysed may be provided by a liquid mobile phase and/or a liquid elution of a stationary phase.

Alternatively or additionally, the proportion of undesired or substances incorrectly coupled to TNS can be determined in a further selection step. The undesired substances are thereby marked by a break-off reaction using a termination reagent which comprises the same reactive group as the substance building blocks of the preceding reaction step. Hence the termination reagent can react with still unreacted precursor molecules and mark these so that the termination reagent can also be termed marker substance. A marker substance can have, for example, in order to enable coupling to a stationary phase, an RNA- or DNA sequence, a biotin- or streptavidin/avidin molecule and/or an azide/alkyne.

The thus prepared substance mixture can then be brought in contact in the form of a mobile phase with a stationary phase in which corresponding collector domains, conjugates, RNA- and/or DNA sequences for coupling the marker substance are immobilised, the undesired substances being able to be bound to the stationary phase, determined and/or quantified. As marker-collector system, there are possible for example the biotin-streptavidin/avidin-, the DNA/DNA-, the RNA/RNA- or the aside-alkyne-Huisgen click reaction.

The previously described selection steps can be effected in particular subsequent to a first sequencing of a substance mixture to be analysed. For this purpose, TNS or TNS-coupled substances, identified already in a first sequencing step, can be removed from the substance mixture to be analysed. Furthermore, consequently also isolation of TNS or TNS-coupled substances can be achieved. Hence further TNS which are present in a lower quantity can be identified by renewed sequencing of the remaining substance mixture. One or more selection step(s) for selection of at least one TNS or TNS-coupled substances can therefore be provided in order to prepare the substance mixture to be analysed.

With respect to the sequencing method to be used—for sequencing a substance mixture to be analysed—no restriction is prescribed. Preferably, a sequencing according to Sanger using fluorescence-marked dideoxynucleotides, at least one polymerase and at least one primer which is complementary to a sequence portion of at least one TNS can be implemented.

Subsequently, the method according to the invention is explained in more detail with reference to embodiments and application examples, in conjunction with the FIGS., There are thereby shown:

FIG. 1: an example of an algorithm for in silica generation of different target nucleotide sequences (TNS)

FIG. 2: an example of a selection step for the selection of TNS

FIG. 3: an example of a deconvolution of a sequence spectrum according to the prescribed algorithm FIG. 4a/b: a schematic diagram of an application example of the method according to the invention In FIG. 1, generation of different tax-get nucleotide sequences (TNS) is illustrated with an example. Generation of the TNS is effected according to the algorithm X in silica. Firstly, the length of the TNS to be formed is established by specification of the sequence positions. In the present case, the sequence length is 14 positions $N_0$-$N_{13}$, an operation z, a, d, or e being prescribed for each sequence position $N_0$-$N_{13}$. At the sequence position $N_0$ with the operation z, no restrictions for a nucleotide A, C, G, T are prescribed. For each further sequence position $N_1$-$N_{13}$, respectively after operations a, d or e, a restriction related to a nucleotide A, C, G, T of a preceding sequence position is prescribed for respectively two nucleotides A, C, G or T. The algorithm X has the form z-a-a-d-d-e-a-a-d-d-e-a-d-e. A selection of thus formed TNS can be deduced from the code table appended in the annex (see p. 16 to 22 in the description). As can be seen from the table with the reference number 10 in FIG. 1, an arbitrarily selected (generated) TNS pair has at least six sequence differences.

Not illustrated, the possibility exists for expanding/developing the thus formed TNS with further sequence positions, by means of which further information can be stored (coded). Thus additional sequence positions or sequence portions can be provided, which respectively code properties of substances to be coupled, such as for example a substance group, substance size, geocoordinates of an exposure location or a date. Furthermore, also supplementary sequence positions can be provided, by means of which the TNS can be identified as such. Generically similar TNS should thereby have the same sequence lengths.

Subsequently, an in vitro synthesis of the TNS generated in silica is implemented by means of the phosphite triester method.

The chemical coupling of the synthesised TNS to the substance representing them can be effected by means of formation of an amide bond with the assistance of peptide coupling reagents.

FIG. 2 shows an example of a selection step in which, in a first sequencing, TNS can be identified as enriched and removed from a mixture. As a result, it is made possible that further TNS can be identified by sequencing, which TNS have been concealed, because of their lower number in the substance mixture (and hence connected lower signal intensity), during the first sequencing by the signal intensity of the frequently occurring TNS. As a result, not only the most enriched TNS but also further TNS enriched to a lesser extent can be identified.

In the present example, a TNS mixture with 11 positions is illustrated on the left-hand side, each position representing a combined TNS, The capital letters thereby represent respectively a single TNS, A stationary phase, on which nucleotide sequences A1', A3', A5', B3', B4' and B9' are immobilised, is characterised with the reference number 20, which nucleotide sequences are complementary to the TNS A1, A3, A5, B3, B4 and B9 and hence enable binding of the mentioned TNS. If the TNS mixture including positions 1 to 11 is brought in contact with the stationary phase 20 as mobile phase, the positions 1 to 9 are bound to the stationary phase 20 and removed from the mobile phase. The TNS mixture (right-hand side) originating from this selection experiment then comprises only the TNS of positions 10 and 11.

FIG. 3 shows a sequence diagram of an example for deconvolution of a sequence spectrum 31 which has been absorbed during sequencing of a substance mixture comprising nucleic acid. In the present example, the sequencing was implemented according to Sanger using fluorescence-marked dideoxynucleotides. On the basis of the signal intensity of the dideoxynucleotides, a relative frequency for the nucleotides A, G, C, T at the respective sequence positions $N_0$-$N_{13}$ in the sequence spectrum 31 could be determined, which relative frequency is illustrated in the form of bars. Because of the frequency distribution of the respective nucleotides at the sequence positions $N_0$-$N_{13}$, different TNS candidates which are possible for an identification can be derived from the sequence spectrum 31, In the present example, the TNS candidates 321 and 322 were determined. These are scanned and deconvoluted by means of the prescribed algorithm X with the operational sequence
z-a-a-d-d-e-a-a-d-d-e-a-d-e
Because of the deconvolution, two TNS 331 and 332 can be identified, TNS 331 representing the substance i and TNS 332 the substance ii.

FIG. 4a shows a schematic diagram of an application example of TNS-coupled substances. According to the embodiment, the propagation of TNS-coupled or TNS-marked particles in the environment should be understood. For this purpose, particles coupled with TNS-A1B3 at position X, particles with TNS coupling A3B4 at position Y and particles with TNS coupling A8B7 at position 7 are exposed. The particles concern for example pollutant particles with a size in the range of 10 nm to 100 µm. The respective positions X, Y or Z, at which the particles are exposed, are coded in a separate sequence portion of the respective TNS. Furthermore, the TNS can also have a separate sequence portion which codes the exposure date (at the respective position X, Y, Z) of the particle, Sampling can be effected for example at a position L. This can be achieved for example with a corresponding air filter. The particles collected by the air filter are then dispersed in a liquid. The thus prepared substance mixture comprising nucleic acid can subsequently be subjected to a sequencing. It can thereby be advantageous to subject the substance mixture comprising the nucleic acid to be analysed before the sequencing to an amplification by means of PGR, corresponding primers for TNS A1B3, TNS A3B4 and TNS A8B7 being used. In this way, the presence of particles marked by particles TNS A1B3, TNS A3B4 and TNS A3B7 can be determined at the position L, as a result of which migration of the particles from positions X, Y and Z can be understood.

Figure 4B:
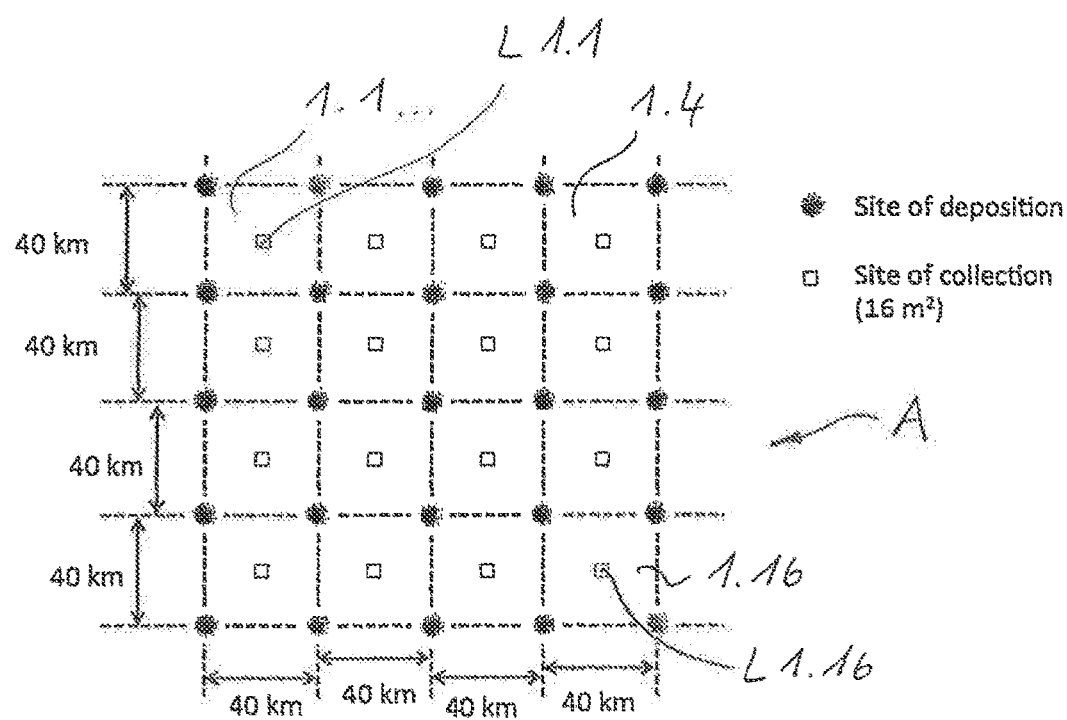

FIG. 4b shows an example of a diagram according to which TNS-marked particles can be exposed and collected, For this purpose, a surface A formed from 16 small squares 1.1-1.16 is illustrated. The edge length of the small squares is for example respectively 40 km so that a surface A in this case has an extension of 1600 km². The points, illustrated in a circle, at the corners of the small squares 1.1-1.16, respectively characterise a location at which TNS-marked particles are exposed, a surface L1.1-L1.16 of at least 16 mm² being provided respectively preferably in the centre in the small squares in order to collect or detect TNS-marked particles.

With the detected TNS-marked particles, a local assignment of the respective position at which one or more TNS-marked particles have been located and analysed can be achieved. This is advantageous in particular if a specific local distribution of TNS-marked particles, which have been moved from one position to other positions as a result of external influences, is intended to be detected.

The described application example can also be adapted to aquatic systems.

A further field of application resides in chemical, biological and medical research. Thus, TNS can be used for example in order to identify molecular structures with specific binding affinities for proteins. Furthermore, also TNS- or DNA-coded chemical molecular libraries can be used effective tool for tracking down ligands for pharmaeeutically relevant proteins. Thus, TNS- or DNA-coded molecules can be enriched for example by an affinity-based selection and subsequently decoded because of their unequivocal TNS- or DNA coding. The TNS- or DNA-coded substance mixtures obtained in such selection experiments can then be deconvoluted easily according to the method according to the invention without isolation/purification or amplification of the mixture being required.

| Annex | | |
|---|---|---|
| Code Table Number (= SEQ ID NO.) | TNS-Code | Round No. |
| 1 | GCGATGAGACATGT | 0 |
| 2 | ATCATATACGTATA | 1 |
| 3 | TAGACATCATAGAG | 2 |
| 4 | TATGTGCTCGCGAG | 3 |
| 5 | AGATGCTATGTCAC | 4 |
| 6 | TCTCGTAGTCTCGT | 5 |
| 7 | TCGATGATCACTCT | 6 |
| 8 | GCTCAGCTGTGCAG | 7 |
| 9 | CTCGAGATCGCTGC | 8 |
| 10 | CGCACTAGATGCGT | 9 |
| 11 | GCTCGCGCGAGCAC | 10 |
| 12 | AGCGTGAGTCTCAG | 11 |
| 13 | CTCGACTATCAGAC | 12 |
| 14 | CGATGCTCATAGTA | 14 |
| 15 | ATCGACGCATGCAG | 15 |
| 16 | GAGTGCGATCAGAG | 17 |
| 17 | CTACACTCACTACA | 18 |
| 18 | TATCGTCGATGATA | 20 |
| 19 | TCTGTATATCTCAC | 21 |
| 20 | GATCACTCGTATCA | 23 |
| 21 | AGCATAGCGACGTA | 24 |
| 22 | TCTGAGCGATAGTA | 25 |
| 23 | ATATCTCTGACGTG | 27 |
| 24 | GAGTCTAGACTCAG | 29 |
| 25 | GAGTGTAGTGTACA | 30 |
| 26 | GCTGTGCTGAGATA | 31 |

Annex

| Code Table Number (= SEQ ID NO.) | TNS-Code | Round No. |
|---|---|---|
| 27 | CTACGTATGTATCT | 32 |
| 28 | TATCGCGACGTATA | 34 |
| 29 | GAGACTCGTGCGTG | 36 |
| 30 | TATCGCTCACAGAC | 37 |
| 31 | TATCGCTACAGCGT | 40 |
| 32 | CTCACTCTCAGCAG | 41 |
| 33 | GATCAGCTCACTGT | 47 |
| 34 | AGCGTGCTGTATGT | 50 |
| 35 | CGACGCGCGACGAG | 52 |
| 36 | TCGATAGACAGATG | 53 |
| 37 | GCGATGCTGTATCA | 54 |
| 38 | CTACGCGATGCTGC | 55 |
| 39 | CGCACAGCACAGTG | 56 |
| 40 | GCGTCAGATGCTCA | 57 |
| 41 | TAGTCTCGATGCGC | 59 |
| 42 | ATCACAGCATGACA | 60 |
| 43 | CTATGCTACACGAC | 68 |
| 44 | CGCACAGATGTCGT | 72 |
| 45 | AGACAGATGAGACT | 74 |
| 46 | ATATCATCGTATGT | 79 |
| 47 | GATGTAGCACTACT | 84 |
| 48 | TATGTATCGACTCT | 88 |
| 49 | CGACAGAGACAGTG | 92 |
| 50 | CTCGTAGATCATGT | 99 |
| 51 | CGACGTCTCGTCGT | 100 |
| 52 | TAGTGCGACGCTCT | 105 |
| 53 | GAGACAGACACTGT | 108 |
| 54 | GCGACTCGATGACA | 109 |
| 55 | AGACACGCGTGATA | 114 |
| 56 | ATCATATCACTCAG | 118 |
| 57 | GATGTATCATATGC | 192 |
| 58 | GCTCGTCGTCAGTA | 124 |
| 59 | CGATGTATCACGTA | 139 |
| 60 | CTATGCTCGTGACT | 140 |
| 61 | TATGTGAGACTATA | 147 |
| 62 | CTCGTGAGTCAGTA | 148 |
| 63 | TCTGACGCGAGACT | 155 |
| 64 | TAGTCTATGACTGC | 161 |
| 65 | CGCGACTATGCTGT | 163 |
| 66 | GATCGTATGTGCGC | 167 |
| 67 | AGATCATACAGACT | 168 |
| 68 | TATGAGCGTGCTGC | 170 |
| 69 | TCGATATATGCTGC | 177 |
| 70 | AGCACTCTCGTATG | 185 |
| 71 | CTATCATATGCGTA | 187 |
| 72 | TCGTGTCGTGCTGT | 197 |
| 73 | GCTGTAGCGTAGTG | 198 |
| 74 | TCTGTGCGTGTACT | 202 |
| 75 | GAGATATCGTGATA | 209 |
| 76 | TCGACTAGACAGTA | 235 |
| 77 | GCGACATATCAGTG | 239 |
| 78 | CGCACTATGTAGTA | 945 |
| 79 | AGCGACGACAGCGT | 261 |
| 80 | CTCATATCGTGCGC | 263 |
| 81 | GAGACTATGAGATG | 270 |
| 82 | GCTCGCTACGTCAG | 295 |
| 83 | CGCACTCGTGCTCA | 299 |
| 84 | GCGTGCTACAGACA | 311 |
| 85 | AGCATGCTCACGAC | 322 |
| 86 | TCGTCAGACACGAC | 325 |
| 87 | AGCGTAGCATAGAC | 330 |
| 88 | TATCAGAGATGCGT | 342 |
| 89 | TCGTCTATCGTCGT | 344 |
| 90 | CTCGACGACACGTA | 360 |
| 91 | AGACACGACGCTCA | 362 |
| 92 | CTATCTCGTCTCAC | 368 |
| 93 | TCTCACTATCATGC | 380 |
| 94 | GCTGAGATCACGAC | 381 |
| 95 | ATATGCGATCATCT | 386 |
| 96 | GCGTGCTCATATCT | 401 |
| 97 | TCTCGTATCGCGTG | 405 |
| 98 | AGATCTCTGTGACA | 414 |
| 99 | GAGATATACGCGAG | 424 |

Annex

| Code Table Number (= SEQ ID NO.) | TNS-Code | Round No. |
|---|---|---|
| 100 | ATCGTGAGATGATG | 437 |
| 101 | TCTCACGCACTATG | 440 |
| 102 | GCGATGCGTGTCAC | 445 |
| 103 | TCGTGTCGATAGAG | 458 |
| 104 | GATCACTATGCGTA | 484 |
| 105 | CTACGTAGTCTATA | 535 |
| 106 | GAGTGCGCACTCGT | 541 |
| 107 | TCGTGCTATGTATG | 542 |
| 108 | AGATGTAGACTACT | 581 |
| 109 | ATACAGAGATATGC | 594 |
| 110 | CTACAGCTCGTATA | 596 |
| 111 | CGACGTCTGAGATG | 608 |
| 112 | CTCGAGCGATGCGC | 625 |
| 113 | TAGATAGATCATCA | 664 |
| 114 | AGCATGCGACTACA | 669 |
| 115 | CGCGAGCTGACTCA | 680 |
| 116 | GATGTAGACGTCGC | 756 |
| 117 | CGCATGATCAGATG | 779 |
| 118 | GCGTCATCGAGCGC | 790 |
| 119 | CTACAGCGTCATCT | 817 |
| 120 | ATACGCGCACTCAC | 893 |
| 121 | CTATGTATGAGCAC | 899 |
| 122 | CTCGTGATGACGAG | 951 |
| 123 | CGCGACGCACATGC | 997 |
| 124 | CTATCAGACGTCAG | 1049 |
| 125 | ATACAGAGTGCGAG | 1112 |
| 126 | ATACGTATCACTGC | 1251 |
| 127 | CGACAGCTCAGCAC | 1311 |
| 128 | CTATCAGCGAGATG | 1355 |
| 129 | ATCACTCGATAGTG | 1376 |
| 130 | CGCATATCATATCT | 1399 |
| 131 | CGCGAGAGTGTACA | 1525 |
| 132 | GAGATGCTGAGCGC | 1568 |
| 133 | AGCATGAGTGCTGT | 1589 |
| 134 | CGCGTAGCGAGCAG | 1778 |
| 135 | AGATCATCATGCAC | 1890 |
| 136 | TCTGTATACACGTA | 1909 |
| 137 | TCTGTATCATGACA | 2169 |
| 138 | TCGTCTCTCAGATA | 2196 |
| 139 | ATACACGATGTATG | 2609 |
| 140 | ATACGCTCGACTCA | 2833 |
| 141 | TCTGACGATGCGAG | 2857 |
| 142 | GATGAGCGTCAGAG | 2910 |
| 143 | GAGTCTCGTCATCT | 3395 |
| 144 | ATACGTAGATGCAG | 3415 |
| 145 | GATCACGATCTCAC | 3428 |
| 146 | ATCACTAGTCATGC | 3651 |
| 147 | TAGTGCGCGTGATG | 3680 |
| 148 | GCTCAGATCGTACT | 4170 |
| 149 | GCTGACTACACTCT | 4243 |
| 150 | AGCGAGAGACATCT | 4391 |
| 151 | TCTCGTCTGACTCT | 4568 |
| 152 | GATGACGCACAGTA | 5440 |
| 153 | ATCACAGATGCGAC | 5554 |
| 154 | GCGACTCTCGCTGC | 5938 |
| 155 | CGACAGCGATGACA | 7003 |
| 156 | AGATCAGCACATCA | 7229 |
| 157 | GCTGTGAGATGCAC | 7364 |
| 158 | GCGATAGCATGCAG | 8343 |
| 159 | GATCGTAGTGCGAC | 8520 |
| 160 | CTCACATACGCTCT | 8522 |
| 161 | CGATGTCGATATGT | 8744 |
| 162 | ATCACTATGACTCT | 8809 |
| 163 | TCGATAGCGTATGT | 8963 |
| 164 | ATACACTCGTAGAG | 9308 |
| 165 | GCGTGTATGTGACT | 9847 |
| 166 | TATCAGATGACGTA | 10090 |
| 167 | GAGACTCTGTAGAC | 10629 |
| 168 | GCGTGCGCGACGTA | 10690 |
| 169 | TAGTCAGATCTCGC | 11570 |
| 170 | AGACAGCGACTCGT | 12132 |
| 171 | CGATCAGATCAGAC | 12906 |
| 172 | GATGACGACAGATG | 13442 |

Annex

| Code Table Number (= SEQ ID NO.) | TNS-Code | Round No. |
|---|---|---|
| 173 | AGCGAGATGTGCAC | 13445 |
| 174 | GCGTCAGCACTATA | 13898 |
| 175 | AGCGTATACACTGC | 14072 |
| 176 | CTCATGCTGTGACT | 15131 |
| 177 | GAGATGATCGTATA | 15693 |
| 178 | TATGACTATCTACT | 16035 |
| 179 | TAGATGATGTAGTG | 17311 |
| 180 | TCGACATCACTCGT | 19265 |
| 181 | GCTGACTCACTCGC | 19811 |
| 182 | GAGTGTCTCGTCAC | 19988 |
| 183 | CGACACTCGAGCGT | 21276 |
| 184 | TATCACGCGACTGC | 21882 |
| 185 | AGATGTATGTAGAG | 21955 |
| 186 | AGACGTCGACAGAC | 22214 |
| 187 | ATCGAGCTCGTCAG | 22328 |
| 188 | TCTGAGATGTATGC | 25668 |
| 189 | AGCGACTCGACGAC | 25671 |
| 190 | GAGACATATGTACT | 31084 |
| 191 | GCTGTGAGTGCGTG | 34906 |
| 192 | CTCATGCGTCTCGT | 34923 |
| 193 | TATGACTCGTGCAC | 42593 |
| 194 | AGACGCTCACATGT | 43050 |
| 195 | CGCGTAGATGCGTG | 48624 |
| 196 | CTACACGACAGACT | 50109 |
| 197 | CGATGTCGTGCGAG | 66603 |
| 198 | TAGATGCGACAGAC | 93912 |

The invention claimed is:

1. Method for the preparation, sequencing, and deconvolution of substance mixtures comprising nucleic acid and identification of the sequence of the nucleic acid, in which
  a) a plurality of target nucleotide sequences (TNS) ($A_1$-$A_n$, $B_1$-$B_n$, ..., $Z_n$), which differ from each other, with $N_0$-$N_n$ sequence positions, are generated from a plurality of nucleotides (A, C, G, T/U), according to a prescribed algorithm, of which
  b) respectively at least one TNS ($A_1$-$A_n$, $B_1$-$B_n$, ..., $Z_n$) is assigned respectively to at least one substance or substance combination and coupled chemically by covalent bonding with the latter, wherein the substance is selected from the group consisting of molecules, molecule components, pollen particles, bacteria particles, and virus particles, and
  c) at least one substance mixture to be analysed, with at least two different TNS-coupled substances contained therein, is prepared, which at least one substance mixture
  d) is sequenced according to a sequencing method, all of the TNS ($A_1$-$A_n$, $B_1$-$B_n$, ..., $Z_n$) contained in the substance mixture being detected in a common sequence spectrum at the same time,
  e) the sequences superimposed in the sequence spectrum being deconvoluted by scanning the sequence positions $N_0$-$N_n$ according to the prescribed algorithm and being identified according to their assignment,
  wherein the prescribed algorithm is $N_0$-$N_{13}$ operational algorithm z-a-a-d-d-e-a-a-d-d-e-a-d-e, where
  z is A/C/G/T,
  a is G/T when z is A, G/T when z is C, A/C when z is G, and A/C when z is T,
  d is C/T when z is A, A/G when z is C, A/T when z is G, and C/G when z is T, and
  e is C/G when z is A, A/T when z is C, C/T when z is G, and A/G when z is T.

2. Method according to claim 1, characterised in that sequence positions $N_0$-$N_n$, which have a significantly increased signal intensity of individual nucleotides (A, C, G, T/U) in the sequence spectrum, are scanned according to the prescribed algorithm.

3. Method according to claim 1, characterised in that significantly increased signal intensities of individual nucleotides (A, C, G, T/U) in the sequence spectrum are subtracted step-wise until the smallest detectable signal intensity is reached at every sequence position $N_0$-$N_n$ for at most one nucleotide (A, C, G, T/U), the thereby obtained subtraction spectra, which have respectively at least sequence portions or sequence fragments, being scanned at the sequence positions $N_0$-$N_n$ according to the prescribed algorithm.

4. Method according to claim 1, characterised in that the TNS ($A_1$-$A_n$, $B_1$-$B_n$, ..., $Z_n$) differ from each other at least two sequence positions and/or by at least one nucleotide sequence consisting of at least five sequence positions.

5. Method according to claim 1, characterised in that the TNS ($A_1$-$A_n$, $B_1$-$B_n$, ..., $Z_n$) are formed with a length of at least five sequence positions.

6. Method according to claim 1, characterised in that the TNS ($A_1$-$A_n$, $B_1$-$B_n$, ..., $Z_n$) have at least one sequence portion, by means of which they can be identified as TNS.

7. Method according to claim 1, characterised in that the TNS ($A_1$-$A_n$, $B_1$-$B_n$, ..., $Z_n$) are single- or double-stranded RNA- or DNA molecules.

8. Method according to claim 1, characterised in that the TNS ($A_1$-$A_n$, $B_1$-$B_n$, ..., $Z_n$) are bonded covalently to the substance(s) assigned to them.

9. Method according to claim 1, characterised in that at least one method step for selection of at least one of the TNS ($A_1$-$A_n$, $B_1$-$B_n$, ..., $Z_n$) and/or at least one TNS-coupled substance is implemented, a substance mixture to be analysed is provided by a liquid mobile phase and/or a liquid elution of a stationary phase.

10. Method according to claim 1, characterised in that the substance mixture to be analysed is sequenced using fluorescence-marked dideoxynucleotides, at least one polymerase and at least one primer which is complementary to a sequence portion of at least one TNS ($A_1$-$A_n$, $B_1$-$B_n$, ..., $Z_n$).

* * * * *